US011866381B2

(12) United States Patent
Efrati et al.

(10) Patent No.: US 11,866,381 B2
(45) Date of Patent: *Jan. 9, 2024

(54) LIGHTWEIGHT APPLIANCE WITH EXOSKELETAL SUPPORT RESPECTIVE KIT-OF-PARTS AND METHOD FOR PRODUCTION OF BIOGAS AND LIQUID FERTILIZER

(71) Applicant: HOME BIOGAS LTD, Beit Yanai (IL)

(72) Inventors: Oshik Moshe Efrati, Beit Yanai (IL); Yair Teller, Clil (IL); Erez Lanzer, Cfar Chaim (IL); Shoham Zak, Givat Ela (IL)

( * ) Notice: Subject to any disclaimer, the term of this patent is extended or adjusted under 35 U.S.C. 154(b) by 757 days.

This patent is subject to a terminal disclaimer.

(21) Appl. No.: 16/622,084

(22) PCT Filed: Jun. 25, 2018

(86) PCT No.: PCT/IB2018/054643
§ 371 (c)(1),
(2) Date: Dec. 12, 2019

(87) PCT Pub. No.: WO2019/003075
PCT Pub. Date: Jan. 3, 2019

(65) Prior Publication Data
US 2021/0188728 A1 Jun. 24, 2021

Related U.S. Application Data

(63) Continuation of application No. 15/632,367, filed on Jun. 25, 2017, now Pat. No. 10,519,071.

(51) Int. Cl.
*C05F 17/964* (2020.01)
*C05F 17/40* (2020.01)
(Continued)

(52) U.S. Cl.
CPC .............. *C05F 17/964* (2020.01); *C02F 3/28* (2013.01); *C02F 11/04* (2013.01); *C05F 9/02* (2013.01);
(Continued)

(58) Field of Classification Search
None
See application file for complete search history.

(56) References Cited

U.S. PATENT DOCUMENTS

| 4,100,023 A | 7/1978 | McDonald |
| 4,169,048 A | 9/1979 | Albers, Sr. |

(Continued)

FOREIGN PATENT DOCUMENTS

| CA | 2731439 | 8/2012 |
| CN | 201309934 Y | 9/2009 |

(Continued)

OTHER PUBLICATIONS www.build-a-biogas-plant.com/biogas-kits.
(Continued)

*Primary Examiner* — William H. Beisner
(74) *Attorney, Agent, or Firm* — Mark David Torche; Patwrite Law

(57) ABSTRACT

An assemblage appliance and method of recycling organic waste into biogas and liquid fertilizer, implementing essentially anaerobic digestion processes, is described. The assemblage appliance includes: a pliant structured exoskeletal envelope, pliable collapsible anaerobic digester and gas tank. A compact kit-of-parts for assembling the aforementioned appliance and respective method using the aforementioned appliance for recycling organic waste into biogas and liquid fertilizer are described.

20 Claims, 11 Drawing Sheets

(51) Int. Cl.
    *C05F 17/907*     (2020.01)
    *C05F 17/914*     (2020.01)
    *C05F 17/986*     (2020.01)
    *C05F 17/979*     (2020.01)
    *C05G 5/20*     (2020.01)
    *C02F 3/28*     (2023.01)
    *C02F 11/04*     (2006.01)
    *C05F 9/02*     (2006.01)
    *C12M 1/107*     (2006.01)
    *C12M 1/00*     (2006.01)
    *C12P 5/02*     (2006.01)
    *C02F 103/00*     (2006.01)

(52) U.S. Cl.
    CPC ............ *C05F 17/40* (2020.01); *C05F 17/907* (2020.01); *C05F 17/914* (2020.01); *C05F 17/979* (2020.01); *C05F 17/986* (2020.01); *C05G 5/20* (2020.02); *C12M 21/04* (2013.01); *C12M 23/26* (2013.01); *C12M 23/36* (2013.01); *C12P 5/023* (2013.01); *C02F 2103/002* (2013.01); *Y02A 40/20* (2018.01); *Y02E 50/30* (2013.01); *Y02P 20/145* (2015.11); *Y02W 10/37* (2015.05); *Y02W 30/40* (2015.05)

(56) References Cited

U.S. PATENT DOCUMENTS

| | | | |
|---|---|---|---|
| 4,632,692 | A | 12/1986 | Lebesgue et al. |
| 5,316,387 | A | 5/1994 | Polett et al. |
| 5,651,890 | A | 7/1997 | Trost |
| 6,375,838 | B1 | 4/2002 | Malige et al. |
| 6,887,374 | B2 | 5/2005 | Humphrey et al. |
| 7,186,339 | B1 * | 3/2007 | Roos ............... A01C 3/023 210/603 |
| 7,669,727 | B2 * | 3/2010 | Hubbard ............ B65D 61/00 220/9.4 |
| 9,688,585 | B2 * | 6/2017 | Efrati ............... C12M 23/54 |
| 10,510,971 | B2 | 12/2019 | Liu et al. |
| 10,519,071 | B2 * | 12/2019 | Efrati ............... C12P 5/023 |
| 2004/0045899 | A1 | 3/2004 | Humphrey et al. |
| 2007/0191527 | A1 | 8/2007 | Mallikarjuna et al. |
| 2008/0131960 | A1 | 6/2008 | Belongia et al. |
| 2010/0316310 | A1 * | 12/2010 | Heater ............. B60K 15/03177 383/119 |
| 2015/0126349 | A1 | 5/2015 | Ishihara et al. |
| 2016/0088788 | A1 | 3/2016 | Wanjihia |
| 2016/0137562 | A1 * | 5/2016 | Efrati ............... C12M 23/14 71/10 |

FOREIGN PATENT DOCUMENTS

| | | |
|---|---|---|
| CN | 201400673 Y | 2/2010 |
| CN | 101337737 B | 8/2010 |
| CN | 201915092 U | 8/2011 |
| CN | 101460413 B | 11/2011 |
| CN | 202022927 U | 11/2011 |
| CN | 202164300 U | 3/2012 |
| CN | 202610224 U | 12/2012 |
| CN | 203320016 U | 12/2013 |
| CN | 102518599 | 1/2016 |
| CN | 105473515 | 4/2016 |
| DE | 8304514 U | 5/1986 |
| DE | 202013102297 U1 | 9/2014 |
| EP | 0033724 | 8/1981 |
| FR | 2261205 | 9/1975 |
| FR | 2983848 | 6/2013 |
| GB | 2162195 | 1/1986 |
| WO | 02062497 | 8/2002 |
| WO | 2011133023 A1 | 10/2011 |
| WO | 2010100309 | 7/2013 |
| WO | 2013190361 | 12/2013 |
| WO | 2016038346 A1 | 3/2016 |

OTHER PUBLICATIONS

Household Biogas Digesters—A Review Authors: Karthik Rajendran, Solmaz Aslanzadeh, Mohammad J Taherzadeh Publication data: Energies,,Dec. 8, 2012,M D P I AG, CH Source info: vol. 5, Nr: 12, pp. 2911-2942.

* cited by examiner

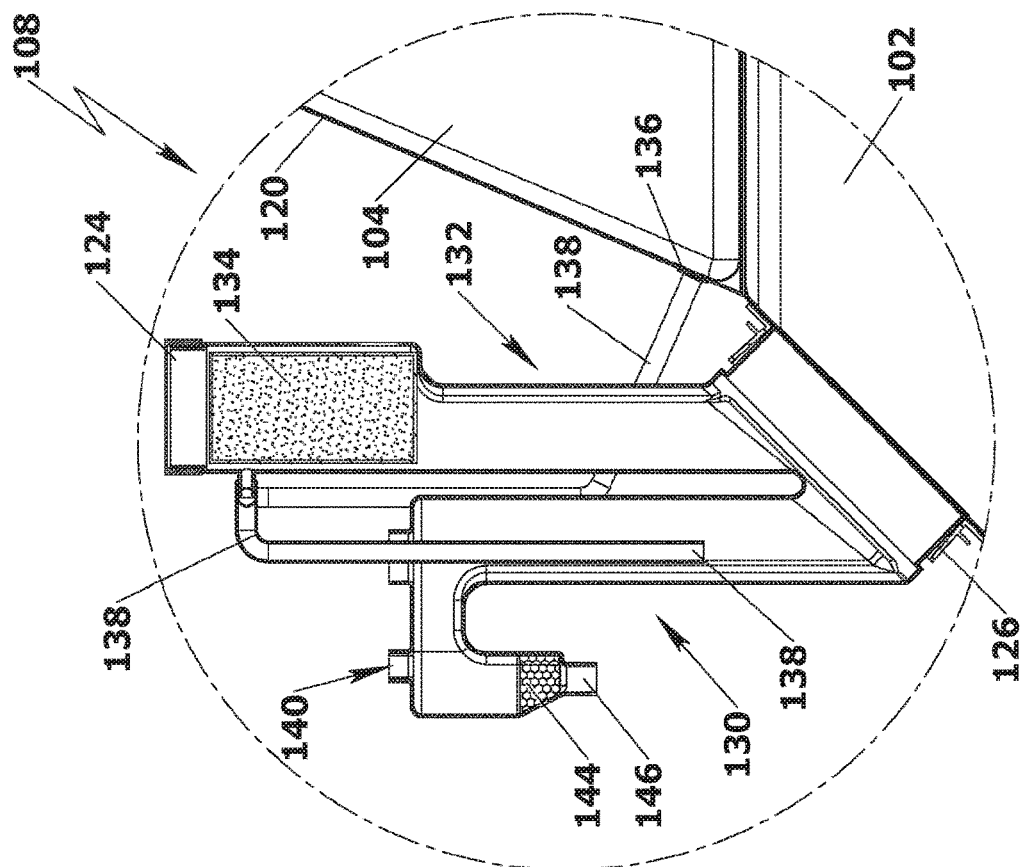
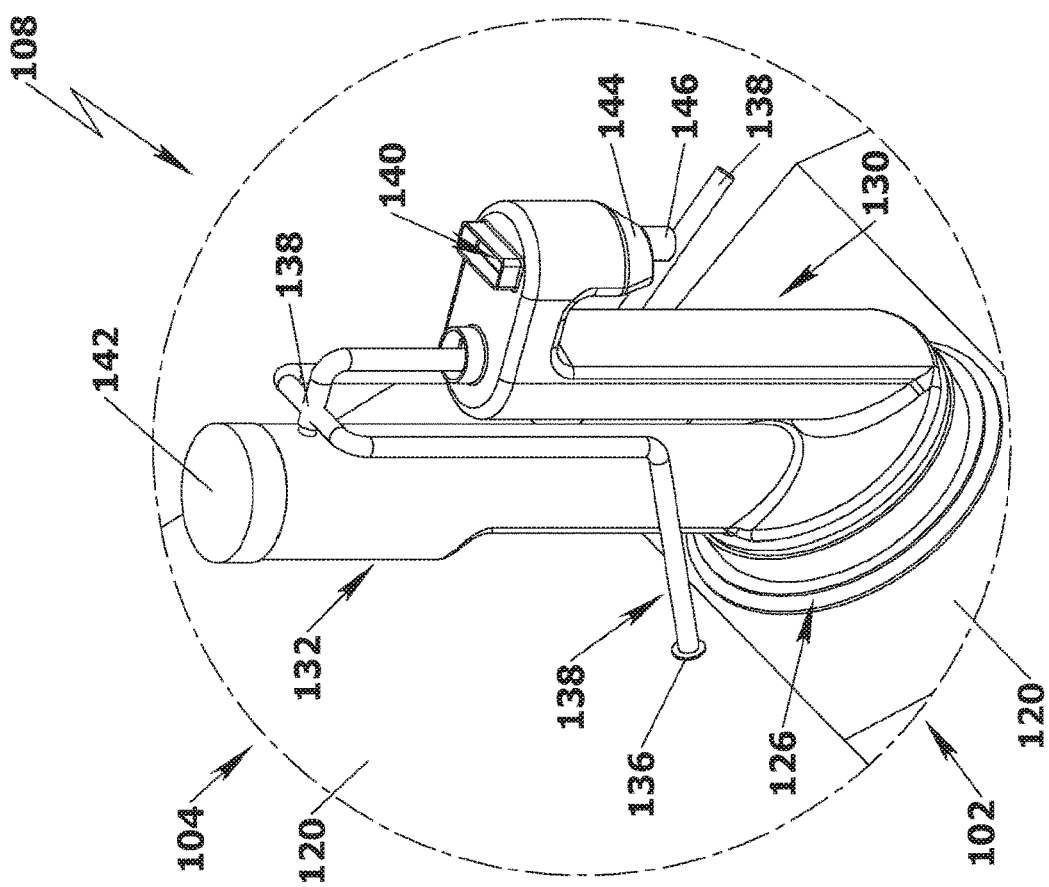

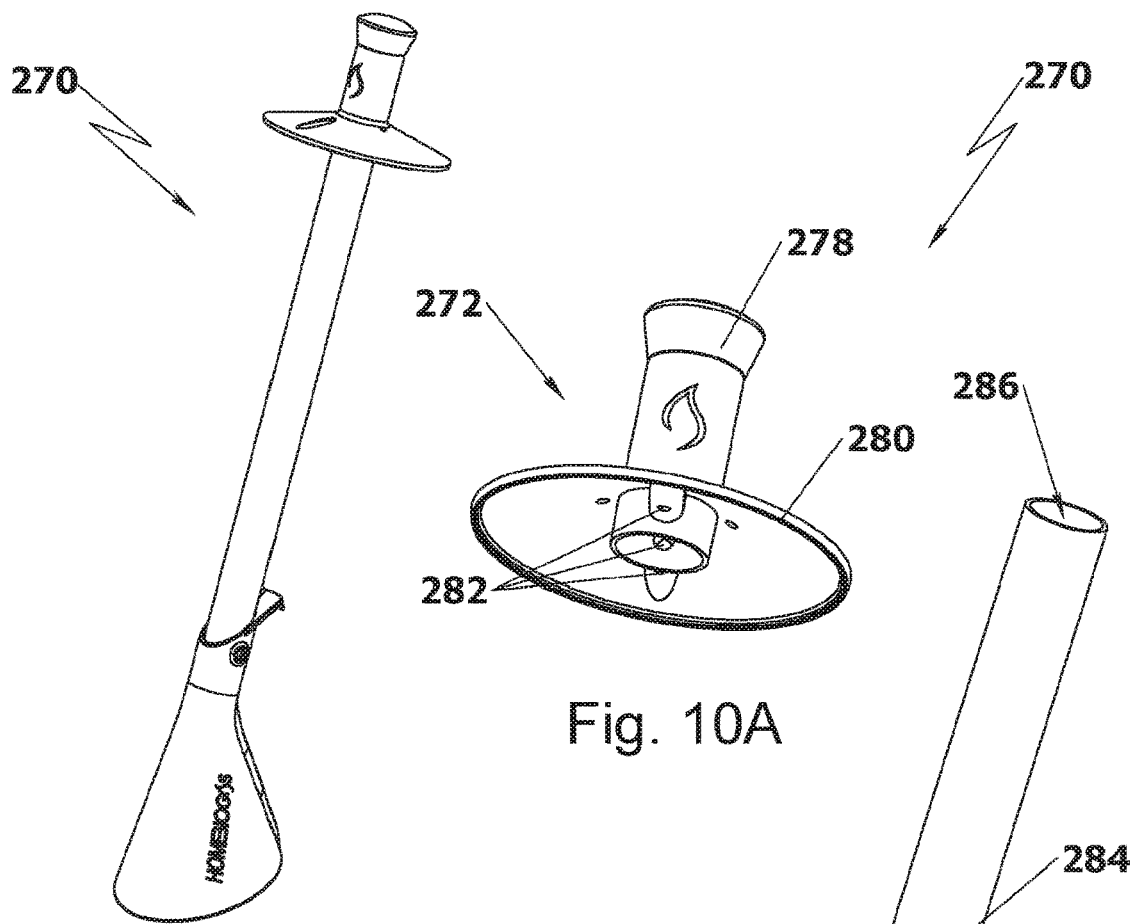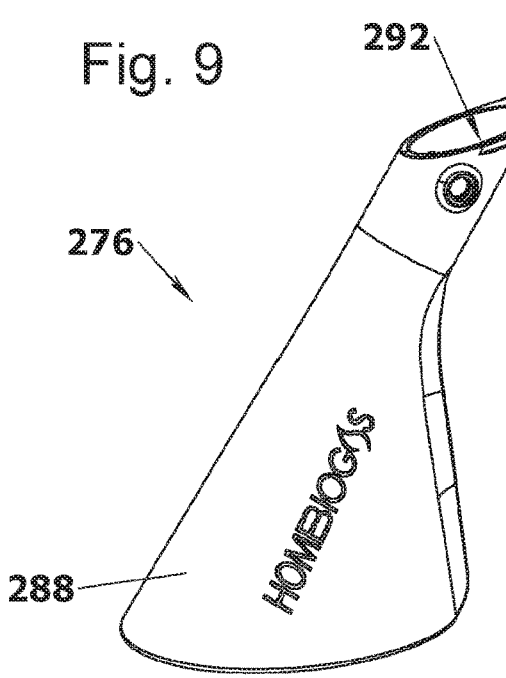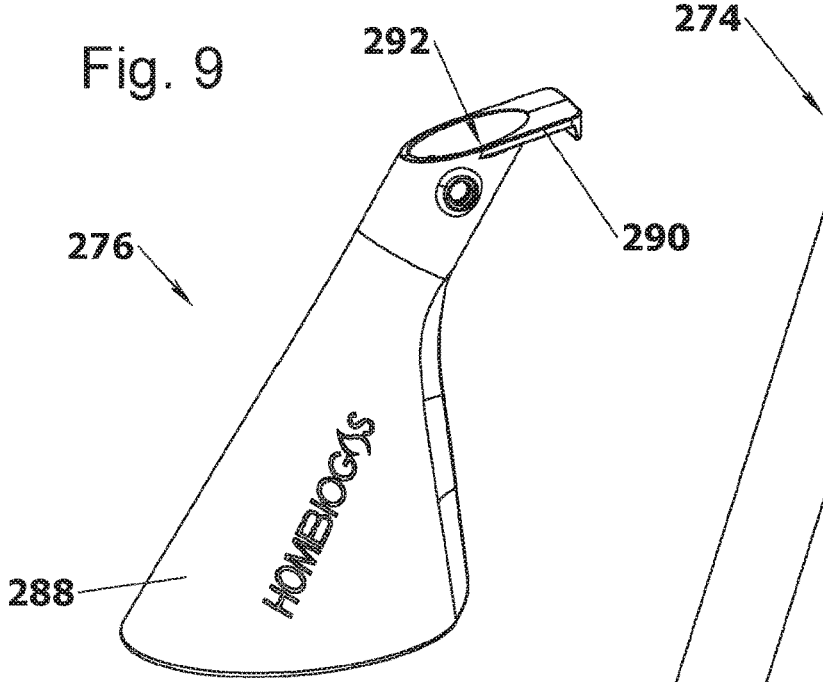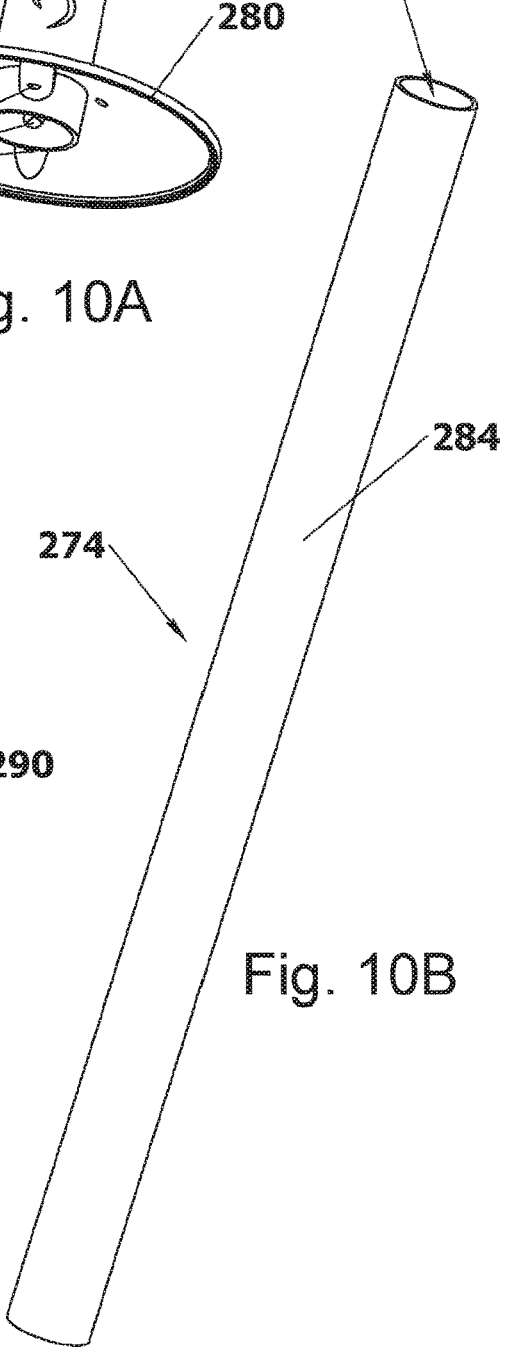

LIGHTWEIGHT APPLIANCE WITH EXOSKELETAL SUPPORT RESPECTIVE KIT-OF-PARTS AND METHOD FOR PRODUCTION OF BIOGAS AND LIQUID FERTILIZER

TECHNICAL FIELD

In general, the present invention pertains to systems and methods of recycling organic waste and utilizing the products thereof. In particular, the invention relates to an extremely lightweight assemblable appliance, supported and shaped by a pliant structured exoskeletal envelope, implementable for recycling organic waste, implementing essentially anaerobic digestion processes.

BACKGROUND ART

Household organic waste makes up a considerable percentage of total waste. This waste is typically thrown out with the rest of the garbage, requiring transport and space in dumps. Such waste is occasionally used for the purposes of producing compost, saving the transport and space requirements, as well as providing a source of rich soil. Hence improved system and methods for combined biogas and fertilizer production from such waste organic waste shall entail an environmental benefit.

Previous attempts include method and device, disclosed in international patent application PCT/ES2010/070120, publication number WO/2010/100309, used for the recycling and exploitation of biodegradable domestic waste produced in the dwellings of a community, by means of prefabricated biogas-production plants, in order to produce electricity and fertilizer and to heat water. The waste is ground in a grinder provided in the kitchen sinks and is conveyed, by means of a network separate from the sewage network, to a biogas-production plant formed by digesters, where biogas is produced by means of anaerobic digestion.

Yet previous attempts include method and device, disclosed in US2010/233778, for generating biogas from organic materials having a biogas reactor which has a charging chamber for being charged with the organic materials and a backflow channel for an at least partial discharge of the organic materials from the biogas reactor. According to US2010/233778 the biogas reactor in addition has at least one intermediate chamber, the charging chambers of which form at least one intermediate chamber and the backflow channel form in this sequence sections of a flow path through which flow can pass in only one direction for the organic materials, two sequentially following sections respectively forming a rising flow path in one case and a falling flow path in the other.

US2015/126349 which is believed to be the most pertinent prior art discloses a method for sealing and cutting of a flexible material for forming a flexible container comprising a product volume and at least one structural support volume can include feeding at least two flexible material into a sealing apparatus comprising a sealing surface and an opposed anvil surface; contacting a seam region of the at least two flexible material with the sealing surface to form a seal in the seam region and cut the seal to form a seam in a single unit operation. The seal in US2015/126349 defines one or both of at least a portion of a boundary of the product volume and at least a portion of a boundary of the at least one structural support volume.

It is further believed that the current state of the art is represented by U.S. Pat. Nos. 2,638,951, 5,429,437, 4,565, 552, 5,924,461, 7,036,676, 7,186,339 and 9,688,585; European patent EP0045114; Chinese patents and utility models CN201575295, CN201400673, CN201915092 and CN202576409, as well as by international patent applications having publication numbers WO2011133023 and WO2012153256.

U.S. Pat. No. 9,688,585 which is believed to be the closest prior art teaches a system and method of recycling organic waste into biogas, implementing an anaerobic digestion processes, is disclosed. The system of U.S. Pat. No. 9,688,585 includes a structural scaffolding and a pliable collapsible anaerobic digester. The aerobic digester in U.S. Pat. No. 9,688,585 includes at least one suspension tab, rendering the anaerobic digester suspendable from the structural scaffolding. A respective kit-of-parts is disclosed by U.S. Pat. No. 9,688,585 for assembling the aforementioned system.

BRIEF SUMMARY

In accordance with one aspect of invention there is provided a lightweight assemblable appliance, forming an autonomic standalone unit, for recycling organic waste into biogas and liquid fertilizer.

In accordance with another aspect of invention there is provided a method of producing biogas and liquid fertilizer by the means of lightweight assemblable appliance, implementing essentially anaerobic digestion processes.

In accordance with yet another aspect of invention there are provided systems and methods of sustaining fluent operation of the aforementioned lightweight assemblable appliance, as an autonomic standalone unit.

In accordance with still another aspect of invention there are provided systems and methods allowing convenient utilization of biogas and liquid fertilizer products resulting the digestion process.

In accordance with yet still another aspect of invention there is provided a lightweight appliance, for recycling organic waste into biogas and liquid fertilizer, assemblable from a compact kit-of-parts, convenient for shipment and deployment.

Definitions

The term assemblable, as referred to herein, is to be construed inter alia as capable of being assembled and deployed, rather readily and promptly, from a kit of respective parts.

The term assemblable, as referred to herein, is to be construed as including disassemblable or capable of being relatively easily dismantled or disassembled for relocation and/or redeployment.

The term assemblable, as referred to herein, is to be construed, inter alia, as providable or capable of being provided in a compact form as well as in dismantled or disassembled form.

Terms and expressions "in a compact form" or alike are to be construed as assuming a final construction size substantially larger than the size of aforesaid compact form.

The terms pliable or pliant, as referred to herein, are to be construed as having high tensile strength and capable of being efficiently flexed or bent but not being resilient and incapable of being efficiently stretched or expanded.

The terms elastic or resilient, as referred to herein, are to be construed as having tensile strength lower than aforesaid tensile strength of pliable or pliant material and optionally being capable of efficiently stretching or expanding.

The term exoskeletal, as referred to herein, is to be construed as being disposed exteriorly and providing structural support and/or firmness.

The term lightweight, as referred to herein, is to be construed as not exceeding 30 kilograms, whereas the term extremely lightweight is to be construed as preferably ranging between 15 and 25 kilograms.

The term compact size, as referred to herein, is to be construed as configured for shipment and transportation at the back seat of an economy car and/or by air cargo.

The terms sheet or fabric, as referred to herein, is to be construed inter alia any spun-melt or non-woven fabrics.

DESCRIPTION OF THE DRAWINGS

The present invention will be understood and appreciated more comprehensively from the following detailed description taken in conjunction with the appended drawings in which:

FIG. 2C is an enlarged view showing details of exemplarily outlet assembly of the lightweight or extremely lightweight assemblable appliance, supported and shaped by a pliant structured exoskeletal envelope;

FIG. 2D is an enlarged cross-sectional view showing details of exemplarily outlet assembly of the lightweight or extremely lightweight assemblable appliance, supported and shaped by a pliant structured exoskeletal envelope;

FIG. 9 is perspective view of a plunger handle;

FIG. 10A to 10C are perspective views of the constituents of the plunger handle;

Figure 1A:
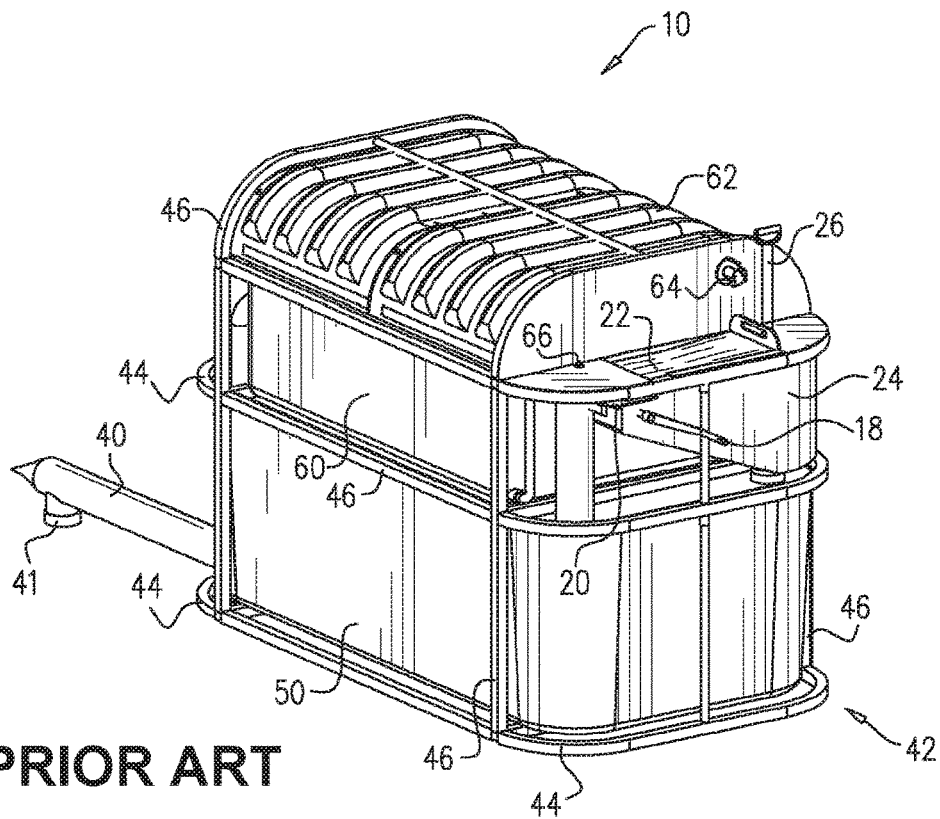
FIG. 1A is a front perspective view of a prior art lightweight assemblable appliance, without the exterior enclosure, according to U.S. Pat. No. 9,688,585.

While the invention is susceptible to various modifications and alternative forms, specific embodiments thereof have been shown merely by way of example in the drawings. The drawings are not necessarily complete and components are not essentially to scale; emphasis instead being placed upon clearly illustrating the principles underlying the present invention.

DETAILED DISCLOSURE OF EMBODIMENTS

Illustrative embodiments of the invention are described below. In the interest of clarity, not all features of actual implementation are described in this specification. It will of course be appreciated that in the development of any such actual embodiment, numerous implementation-specific decisions must be made to achieve the developers' specific goals, such as compliance with technology- or business-related constraints, which may vary from one implementation to another. Moreover, it will be appreciated that the effort of such a development might be complex and time-consuming, but would nevertheless be a routine undertaking for those of ordinary skill in the art having the benefit of this disclosure.

Figure 1B:
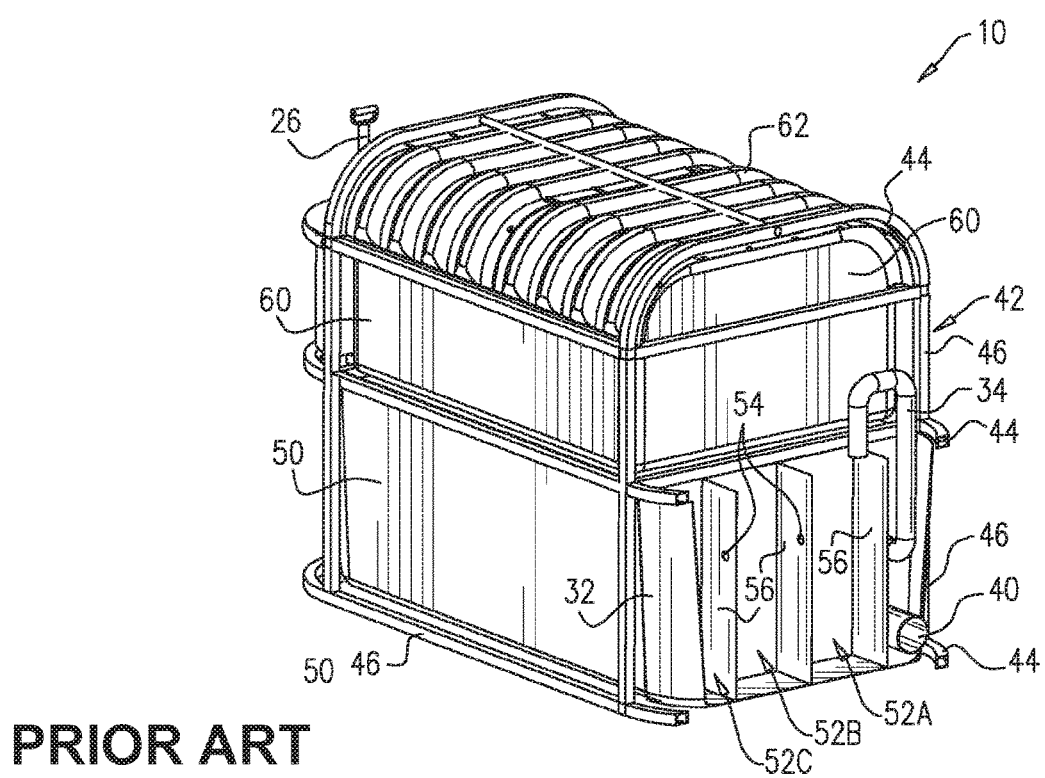
FIG. 1B is a rear perspective view of the prior art lightweight assemblable appliance, shown in FIG. 1A, according to U.S. Pat. No. 9,688,585.

Before elaborating any embodiment of the present invention, reference is firstly made to FIGS. 1A and 1B, which are FIGS. 1C-D of U.S. Pat. No. 9,688,585, showing prior art lightweight assemblable appliance 10. Prior art lightweight assemblable appliance 10 forms an autonomic standalone unit, utilized for recycling organic waste into biogas and liquid fertilizer. Prior art appliance 10 comprises anterior portion 14 and posterior portion 16. Anterior portion 14 and accommodates feeding sub-assembly comprising sink 24, grinder 20 and sink cover 22, as well as optionally fluid canister 28, or a fluid supply hose (not shown) disposed on top of sink 24, furnished with tap 30. Grinder 20 is typically driven either manually, for instance by the means of handle 18. Sink cover 22 is configured for conveniently feeding-in organic waste into grinder 20. The semiliquid mixture or slurry of ground organic matter and fluid is then fed into pliable collapsible anaerobic digester 50 through inlet pipe 27, which is connected to the outlet of sink 24. Inlet pipe 27 employed for feeding the semiliquid mixture or slurry of ground organic matter and fluid into anaerobic digester 50 is hermetically attached to anaerobic digester 50, so that the interior lumen of inlet pipe 27 forming a continuum with interior lumen of anaerobic digester 50. Inlet pipe 27 extends at least through a substantial portion of vertical dimension of anaerobic digester 50.

According to U.S. Pat. No. 9,688,585, multiple structural elements (not shown), such as flanges or pipe fittings, are attached to anaerobic digester 50 surfaces. In one embodiment, at least one inlet pipe 27 and or at least one slurry overflow outlet pipe 34 is/are connected to anaerobic digester 50 with such structural elements (not shown). In an embodiment, gas outlet pipe 59 is connected to anaerobic digester 50 with a structural member. In an embodiment, at least one sludge outlet pipe 40 is connected to anaerobic digester 50 with such a structural element.

According to U.S. Pat. No. 9,688,585, lightweight assemblable appliance 10 comprises posterior portion 16, which includes posterior compartment 32. Posterior compartment 32 forms an integral part of pliable collapsible anaerobic digester 50 or attached to anaerobic digester 50. Posterior compartment 32 may be divided by partitions 56, into sub-compartments 52A, 52B and 52C. Apertures 54 in partitions 56 interconnect between sub-compartments 52A to 52C. Sub-compartments 52A to 52C are configured to encompass overflow of liquid fertilizer or slurry resulting the digestion processes in anaerobic digester 50. Liquid fertilizer or slurry is optionally spilled over, from slurry overflow outlet pipe 34, having a siphon configuration, extending from a sidewall of anaerobic digester 50 into sub-compartment 52A. Sub-compartment 52C may include overflow outlet flange or pipe fitting 37, further furnished with nozzle 36. Sub-compartments 52A to 52C are optionally furnished with sealable drainage apertures 38, for conveniently emptying sub-compartments 52A to 52C upon opening of drainage apertures 38.

Posterior portion 16 further includes a sludge outlet draining pipe 40, extending from a bottom portion of a sidewall of anaerobic digester 50, configured for drainage of sludge and/or slurry resulting the digestion processes in anaerobic digester 50. Sludge outlet draining pipe 40 is preferably furnished with sealable cap or baffle 41, adapted for controllably opening/resealing sludge outlet draining pipe 40. Sludge outlet draining pipe 40 is pliable, allowing elevating the terminal portion thereof, thereby preventing the flow from anaerobic digester 50.

According to U.S. Pat. No. 9,688,585, lightweight assemblable appliance 10 comprises assemblable structural scaffolding 42. Structural scaffolding 42 comprises a plurality of arcuate structural members 44 and a plurality of linear structural members 46, interconnected by connectors 48. Structural scaffolding 42 is assemblable from a compact kit-of-parts comprising arcuate structural members 44, linear structural members 46 and connectors 48. Structural scaffolding 42 is characterized by the compactness of the kit-of-parts used for assembling it; thereby rendering assemblable appliance 10 suitable for shipment and transportation in a rather compact disassembled form. Structural scaffolding 42 comprises at least one structural member adapted for suspending pliable collapsible anaerobic digester 50, as elaborated infra.

According to U.S. Pat. No. 9,688,585, connectors 48 are embodied within terminal portions of structural members 44 and 46 and comprise an integral part of structural members 44 and 46. Structural members 44 and 46 thus interlock within each other, for instance by female and male endings of members 44 and 46; whereby multiple parts are connectable directly, without employing any individual connector 48 parts. Structural members 44 and 46 are profiles designed to provide increased bending strength. A couple of linear structural members 46 may be provided as a singular L-shaped member.

According to U.S. Pat. No. 9,688,585, anaerobic digester 50 is preferably made of at least one sheet of pliable material 51, defining an essentially closed rectangular parallelepiped shaped structure; thereby rendering anaerobic digester 50 pliable and collapsible. Anaerobic digester 50 is manufactured by welding of polymeric sheets. Therefore, anaerobic digester 50 is capable of assuming a collapsed or folded conformation, suitable for shipment and transportation in a rather compact folded form. Anaerobic digester 50 may be manufactured by welding and/or gluing segments polymeric sheets or by a means of molding, such as vacuum molding or blow molding.

According to U.S. Pat. No. 9,688,585, pliable collapsible anaerobic digester 50 shown in FIGS. 1A and 1B comprises elongated suspension tabs 58 attached along edges of anaerobic digester 50. Elongated suspension tabs 58 are attached to the surfaces of anaerobic digester 50. Structural members 46 are threaded into elongated suspension tabs 58, thereby rendering anaerobic digester 50 suspendable from structural scaffolding 42. Upon filling anaerobic digester 50 with the aforementioned semiliquid mixture or slurry of ground organic matter and fluid, while anaerobic digester 50 is suspended from structural scaffolding 42, stability is conferred to the structure of assemblable appliance 10 by the gravitational force exerted onto structural members 46 of scaffolding 42.

The suspension tabs, such as tabs 58, according to U.S. Pat. No. 9,688,585, mat embody a variety of shapes and/or structures as well as optionally include additional elements. The suspension tabs, such as tabs 58 may form an integral part of pliable collapsible anaerobic digester 50. Suspension tabs may include: a ring, an elongated sleeve, an abutment for attachment of another element, an element resembling a lifting ear. Anaerobic digester 50 may be suspended by straps and/or harness-like flexible structure (not shown), which are connected to structural scaffolding 42. In yet another embodiment, tab 58 comprises an extension of anaerobic digester 50 threaded into a slot in structural members 46.

Pliable collapsible anaerobic digester 50, according to U.S. Pat. No. 9,688,585, further comprises gas outlet pipe 59, hermetically attached to an upper face of digester 50 and extending upwardly therefrom. Baffle 70 is connected to gas outlet pipe 59, for controlling distribution of gas accumulated under positive pressure in pliable anaerobic digester 50 as a result of anaerobic digestion processes occurring therein. The gas distribution system may include safety valve 66, coupled to gas outlet pipe 59 and/or baffle 70 by conduit 72. Safety valve 66 is employed to release any excessive pressure of gas from anaerobic digester 50, upon exceeding a predetermined threshold. Gas distribution system further comprises conduit 74, coupling gas tank 60 to gas outlet pipe 59 and/or baffle 70.

According to U.S. Pat. No. 9,688,585, lightweight assemblable appliance 10 comprises a resilient gas tank or bladder 60, employed to accumulate the gas produced by the anaerobic digestion processes tacking place in anaerobic digester 50 under positive pressure for subsequent use. Resilient gas tank 60 is typically disposed on top of anaerobic digester 50. Resilient gas tank 60 may be detached from the structural scaffolding 42 while being connected to anaerobic digester 50 with a gas pipe 74. Resilient gas tank 60 can be made of at least one sheet of pliable and somewhat resilient material 61, defining an essentially closed structure; thereby rendering gas tank 60 collapsible as well as expandable or stretchable. Therefore resilient gas tank 60 capable of assuming a collapsed or depleted conformation, suitable for shipment and transportation in a rather compact folded form.

It is noted that resilient gas tank 60, according to U.S. Pat. No. 9,688,585, can assume a variety of shapes, inter alia cylindrical, semi-cylindrical and a somewhat rectangular shape, optionally having at least a convex upper face. Resilient gas tank 60 comprises inlet 67 coupled by conduit 74 to the gas distribution system. Resilient gas tank 60 further comprises gas outlet faucet 64, configured to allow conveniently utilizing the gas. Lightweight assemblable appliance 10 comprises array 62 of elongated and foldable ballast bags 80. Array 62 of ballast bags 80 is employed to exert gravitational force onto convex upper face of resilient gas tank 60, thereby contributing to the positive pressure of the gas inside gas tank 60 and rendering the gas inside gas tank 60 readily available for utilization. Ballast bags 80 are fillable with ballast substance, typically having a relatively high density or weight to volume ratio, such as sand. An array 62 of ballast bags 80 is capable of assuming an arcuate conformation, respectively conforming the surface of resilient gas tank 60. Array 62 of ballast bags 80 is capable of assuming a conformation, respectively conforming the shape of the top surface of pliable gas tank 60. Ballast bags 80 are disposed on foldable bands 82, which are optionally include apertures 86 along the edges thereof. Interconnecting strips 88 are threaded into apertures 86 to adjoin a plurality of foldable bands 82 in tandem. Fillable ballast bags 80 of array 62 are assuming a depleted conformation, suitable for shipment and transportation in a rather compact folded form. In some embodiment array 62 of ballast bags 80 is connected and/or forms an integral part of resilient gas tank 60.

Figure 2A:
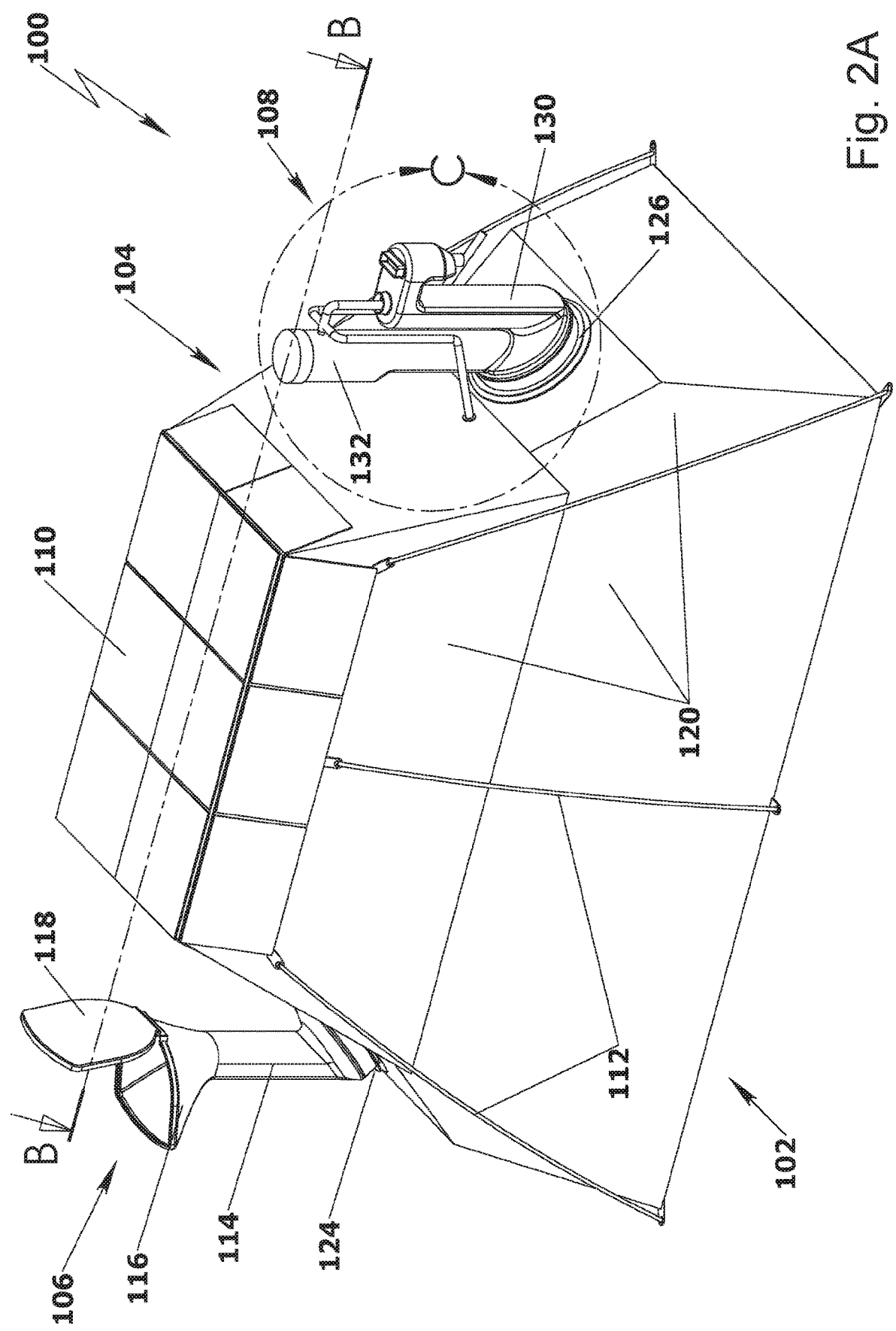
FIG. 2A is an isometric view of a preferred embodiment of the lightweight or extremely lightweight assemblable appliance, supported and shaped by a pliant structured exoskeletal envelope.
Figure 2B:
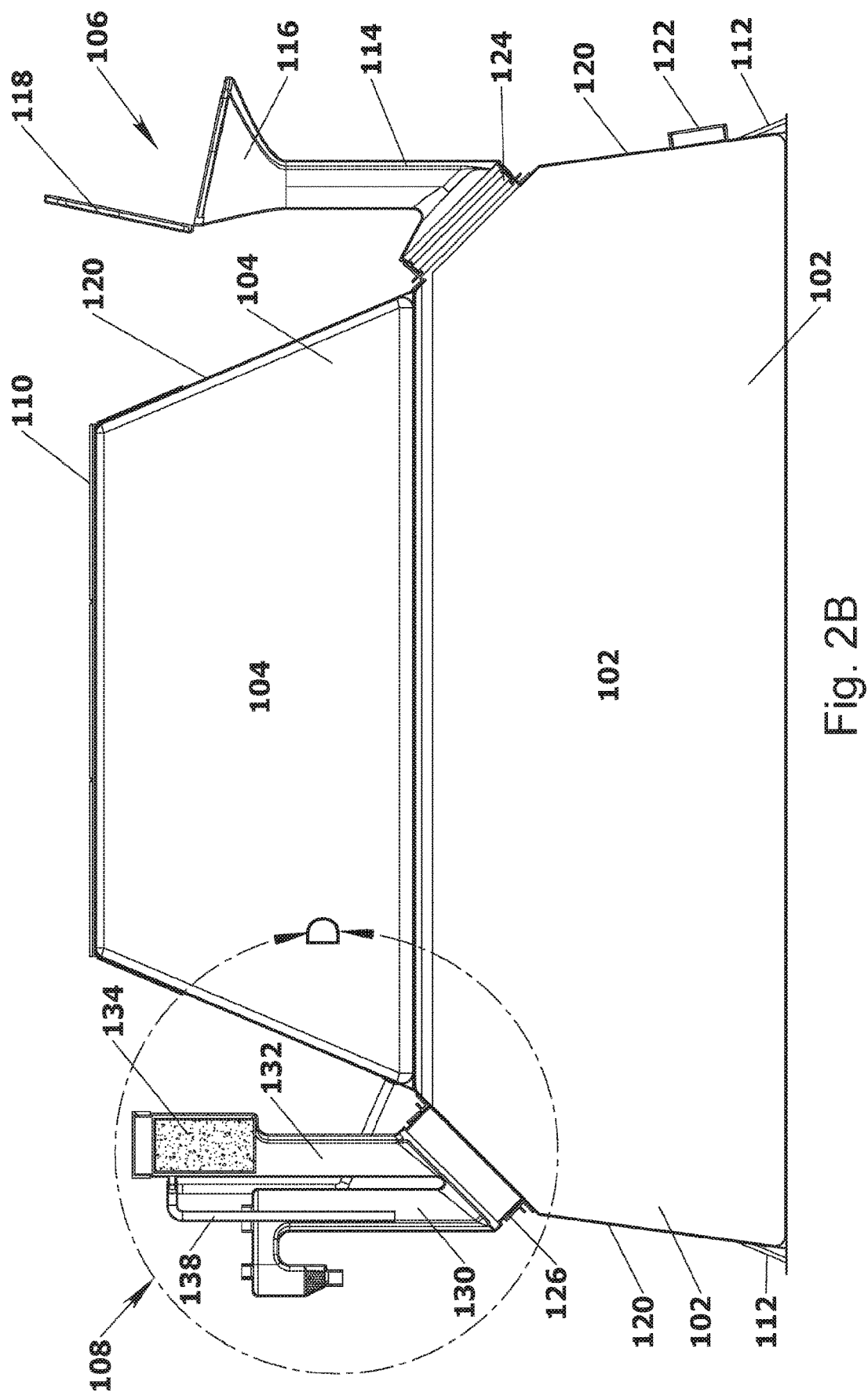
FIG. 2B is a cross-sectional view of a preferred embodiment of the lightweight or extremely lightweight assemblable appliance, supported and shaped by a pliant structured exoskeletal envelope.

In accordance with some preferred embodiments of the present invention, reference is now made to FIGS. 2A and 2B, showing isometric cross-sectional, views of lightweight or preferably extremely lightweight assemblable appliance 100, as well as to FIG. 2C to 2C, showing enlarged and cross-sectional enlarged views of outlet assembly 108. Appliance 100 comprises anaerobic digester 102 and gas tank 104. Digester 102 and tank 104 are made of elastic, resilient or pliable material.

Referring particularly to FIG. 2A to 2B, appliance 100 further comprises pliant structured exoskeletal envelope 120. Pliant structured exoskeletal envelope 120 defines a frusto-pyramidal shape, where anaerobic digester 102 is accommodated at the bottom portion of the pliant structured exoskeletal envelope 120, whereas gas tank 104 is accommodated at the top portion of the pliant structured exoskeletal envelope 120. Pliant structured exoskeletal envelope 120 confines digester 102 and tank 104 and thereby limits the expansion thereof.

Consequently, upon filling-up anaerobic digester 102 with semiliquid mixture or slurry or ground organic matter or any type of fluid for that matter, in a non-limiting manner including water, grey water and slurry overflow fluid, and/or upon forming positive pressure in gas tank 104, pliant structured exoskeletal envelope 120 is expanded and shaped-up by the pressure exerted from within by digester 102 and tank 104, to assume an erected or deployed confirmation, shown in FIGS. 2A and 2B. It is noted that the anaerobic digestion processes, occurring in pliable anaerobic digester 102, resulting a positive pressure in gas tank 104, mainly of methane gas. In some embodiments, organic matter optionally includes for animal droppings, which utilized by lightweight assemblable appliance 100, typically without grinding.

Upon filling-up anaerobic digester 102 with content and forming positive pressure in gas tank 104, pliant structured exoskeletal envelope 120 confers structural firmness to appliance 100, due to a normal counterforce to the force exerted by the faces of digester 102 and tank 104 on exoskeletal envelope 120, somewhat resembling the structural firmness of a wheel tire (not shown) conferred by the expansion of the inner tube (not shown). Pliant exoskeletal envelope 120 embodies a structured shape, configured to accommodate anaerobic digester 102 and gas tank 104, so as to limit their expansion to a maximal predetermined size.

Pliant exoskeletal envelope 120 is preferably made of woven or fibrous fabric, having high tensile strength and capable of being efficiently flexed or bent but incapable of being efficiently stretched or expanded. In some embodiments, pliant structured exoskeletal envelope 120 co-molded or welded with anaerobic digester 102 and/or gas tank 104, to form a monolithic constituent, in which anaerobic digester 102 and/or gas tank 104 are non-detachable pliant structured exoskeletal envelope 120. In other embodiments, pliant structured exoskeletal envelope 120 is an individual constituent distinct from anaerobic digester 102 and/or gas tank 104.

Anaerobic digester 102 comprises anterior flange 124, configured for connecting and mounting anterior inlet assembly 106, implementable for feeding semiliquid mixture, slurry, ground organic matter or a fluid, into anaerobic digester 102. Anterior flange 124 preferably comprises a feeding mechanism, such as a diaphragm or mitral valve (not shown), configured to sustain advancement of semiliquid mixture, slurry, ground organic matter or a fluid, fed into anaerobic digester 102, from anterior inlet assembly 106 but concurrently configured to prevent backflow of the contents from digester 102 into anterior inlet assembly.

Anaerobic digester 102 comprises posterior flange 126, configured for connecting and mounting posterior outlet assembly 108, implementable for draining grey water or overflow slurry fluid from anaerobic digester 102 as well as preferably for conducting the biogas produced by the anaerobic processes in digester 102 to gas tank 104 via conduit 138. Anaerobic digester 102 optionally comprises anterior opening with removable plug 124, configured for occasionally depleting the sludge that may accumulate in digester 102, as a part of maintenance of lightweight assemblable appliance 100. It is, however, noted that anterior opening with removable plug 124, configured for depleting the sludge from digester 102, is merely optional, whereas in some embodiments there is no dedicated opening for depleting the sludge from digester 102.

In order to yet further facilitate an increased pressure inside gas tank 104, appliance 100 further comprises at least one pressure forming mechanism. Embodiments of pressure forming mechanisms in a non-limiting manner include gravitational and/or bias driven devices. Examples of gravitational devices include array of ballast bags or pockets 110, fillable with ballast substance (not shown), configured to facilitate increased pressure by exerting gravitational force onto inside gas tank 104.

Examples of bias driven devices include elastic tension straps 112, comprising an elastomeric material, connected to respective elements attached to the bottom of appliance 100, configured to facilitate increased pressure by exerting tensile strain force onto inside gas tank 104. Notably a combination of gravitational and/or bias driven devices is equally contemplated by this disclosure.

Referring particularly to FIGS. 2C and 2D, anterior inlet assembly 106 comprises feeding conduit 114, which is optionally made of solid, stiff or firm material, capable of supporting its own weight. Feeding conduit 114 terminates with inlet funnel 116, coverable by pivoting and preferably biased lid 118. In some examples feeding conduit 114 is made of flexible or pliant material, incapable of supporting its own weight, in such cases inlet funnel 116 is supported by a bipod (not shown) structure.

Posterior outlet assembly 108 comprises slurry overflow outlet portion 130 and gas ducting portion 132. Slurry overflow outlet portion 130 comprises chlorinator 144, chlorinator filling port 140 and slurry overflow nozzle 146. Slurry overflow nozzle 146 is disposed downstream to chlorinator 144, so that any overflow of slurry from digester 102 to outlet portion 130 passes through chlorinator 144, thereby rendering the fluids outflowing from slurry nozzle 146 non-virulent and biologically safe for the environment or use for irrigation in agriculture.

Gas ducting portion 132 of posterior outlet assembly 108 further comprises biogas filter 134, configured for absorbing sulfurous compounds from the biogas produced in anaerobic digester 102. The biogas filter 134 optionally comprises activated carbon or activated charcoal, which is replaceable from the top opening covered by plug 142. Gas infiltrating through biogas filter 134 is supplied into gas piping 138. Gas piping 138 extends from gas ducting portion 132 of posterior outlet assembly 108 to gas inlet 136 of gas tank 104. Gas piping 138 further extends to a gas-powered consuming appliance (not shown). Gas piping 138 further optionally extends into slurry overflow outlet portion 130. Gas piping further 138 optionally comprises check valves, configured to conduct the biogas only in one direction, and/or safety valves, configured to conduct the biogas only above a predetermined pressure threshold.

Figure 3:
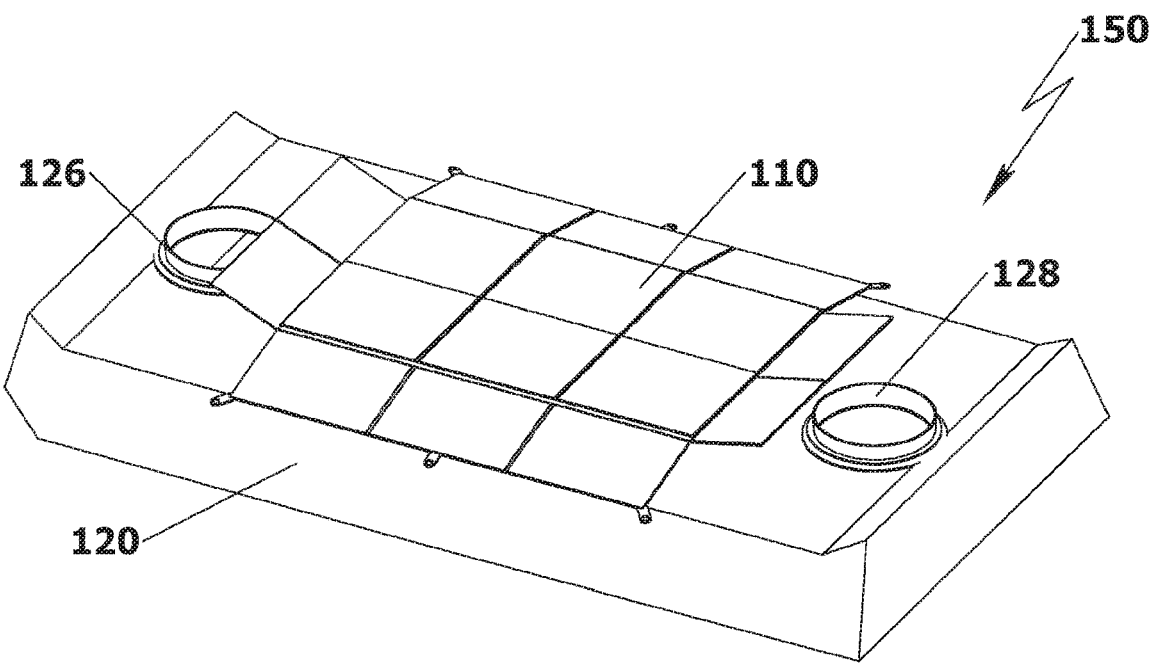
FIG. 3 is an isometric view of a preferred embodiment of the lightweight or extremely lightweight assemblable appliance, in a depleted or collapsed configuration.

Reference is now made to FIG. 3, showing the lightweight or preferably extremely lightweight assemblable appliance in folded or collapsed conformation 150. Lightweight assemblable appliance in folded conformation 150 is configured for assuming a compact size. Lightweight assemblable appliance in folded conformation 150 is typically folded yet further laterally or rolled up to assume a compact size (not shown), configured for shipment and transportation at the back seat of an economy car and/or by air cargo.

Figure 4:
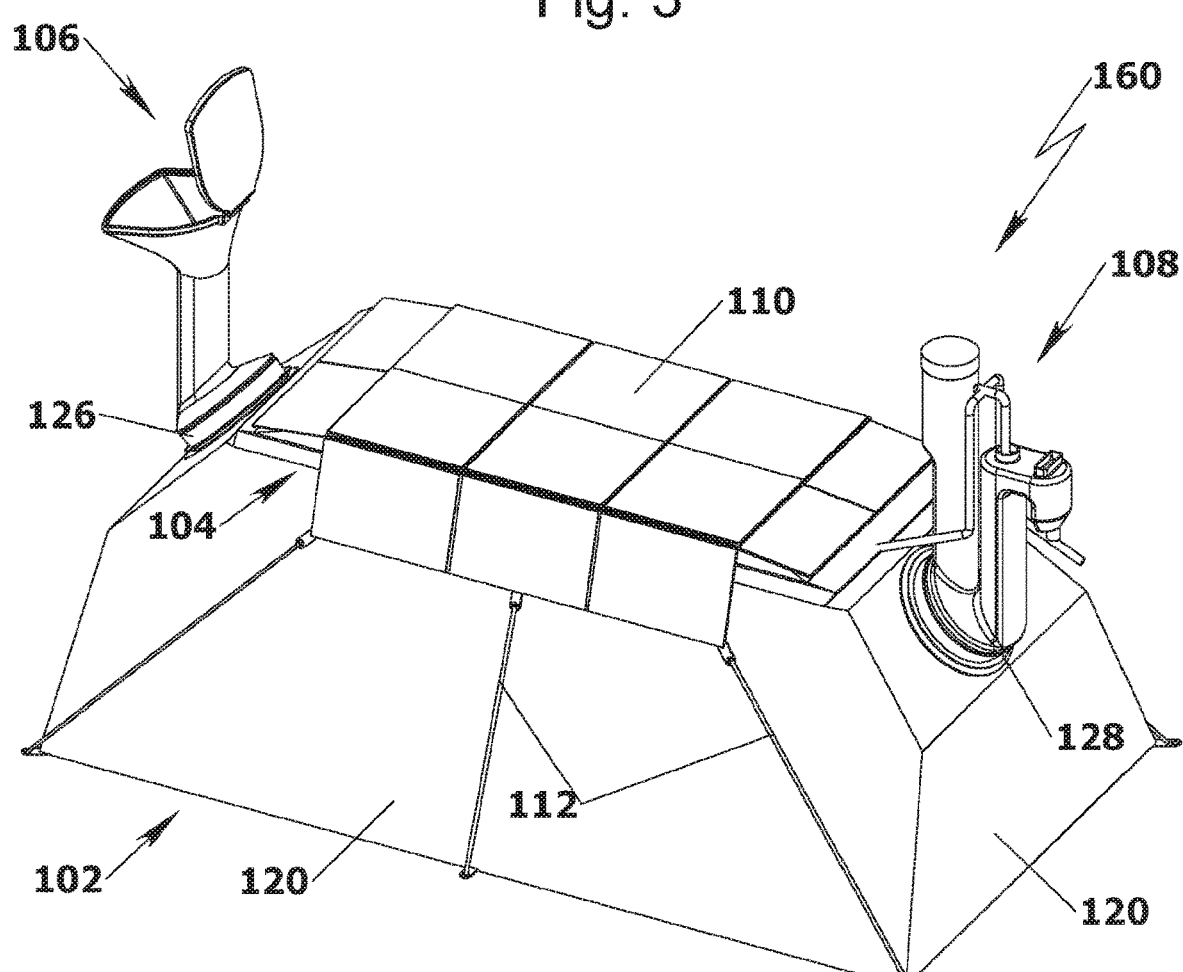
FIG. 4 is an isometric view of a preferred embodiment of the lightweight or extremely lightweight assemblable appliance, wherein the anaerobic digester is in a deployed or erected configuration, whereas the gas tank in a depleted or collapsed configuration.

Reference is now made to FIG. 4, showing the lightweight or preferably extremely lightweight assemblable appliance in a partially erected or deployed conformation 160. Lightweight assemblable appliance assumes a partially erected or deployed conformation 160 upon filling-up anaerobic digester 102 with liquid. Gas tank 104 of lightweight assemblable appliance in a partially erected or deployed conformation 160 is empty of biogas. With the progression of anaerobic processes in anaerobic digester 102, biogas filling-up gas tank 104 and lightweight assemblable appliance assumes completely erected or deployed conformation 100, shown in FIGS. 2A and 2B.

BEST MODE FOR PRACTICING AND CARRYING OUT THE INVENTION

Figure 5:
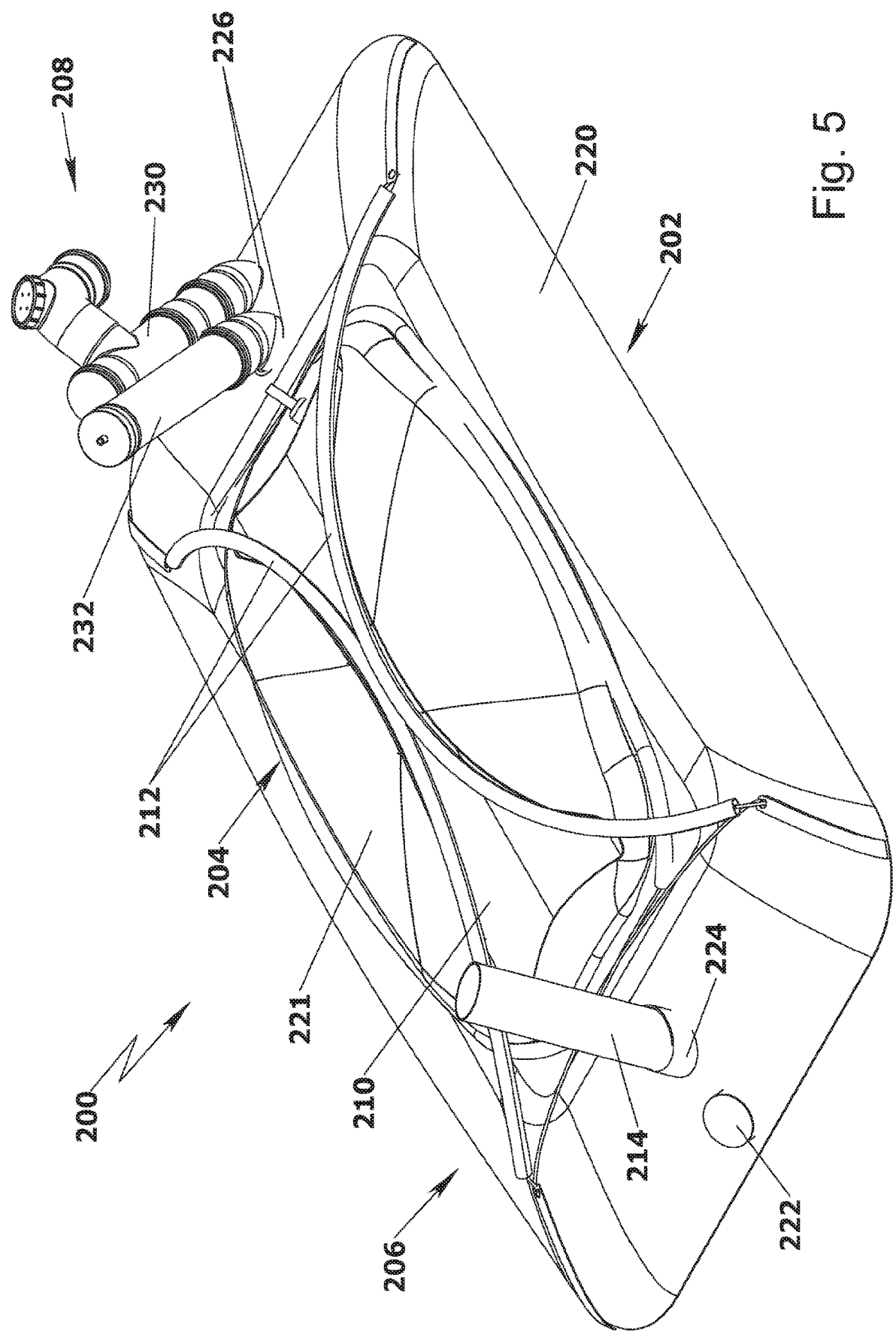
FIG. 5 is an isometric view of a preferred embodiment of the lightweight or extremely lightweight assemblable appliance, in a depleted or collapsed configuration.
Figure 6:
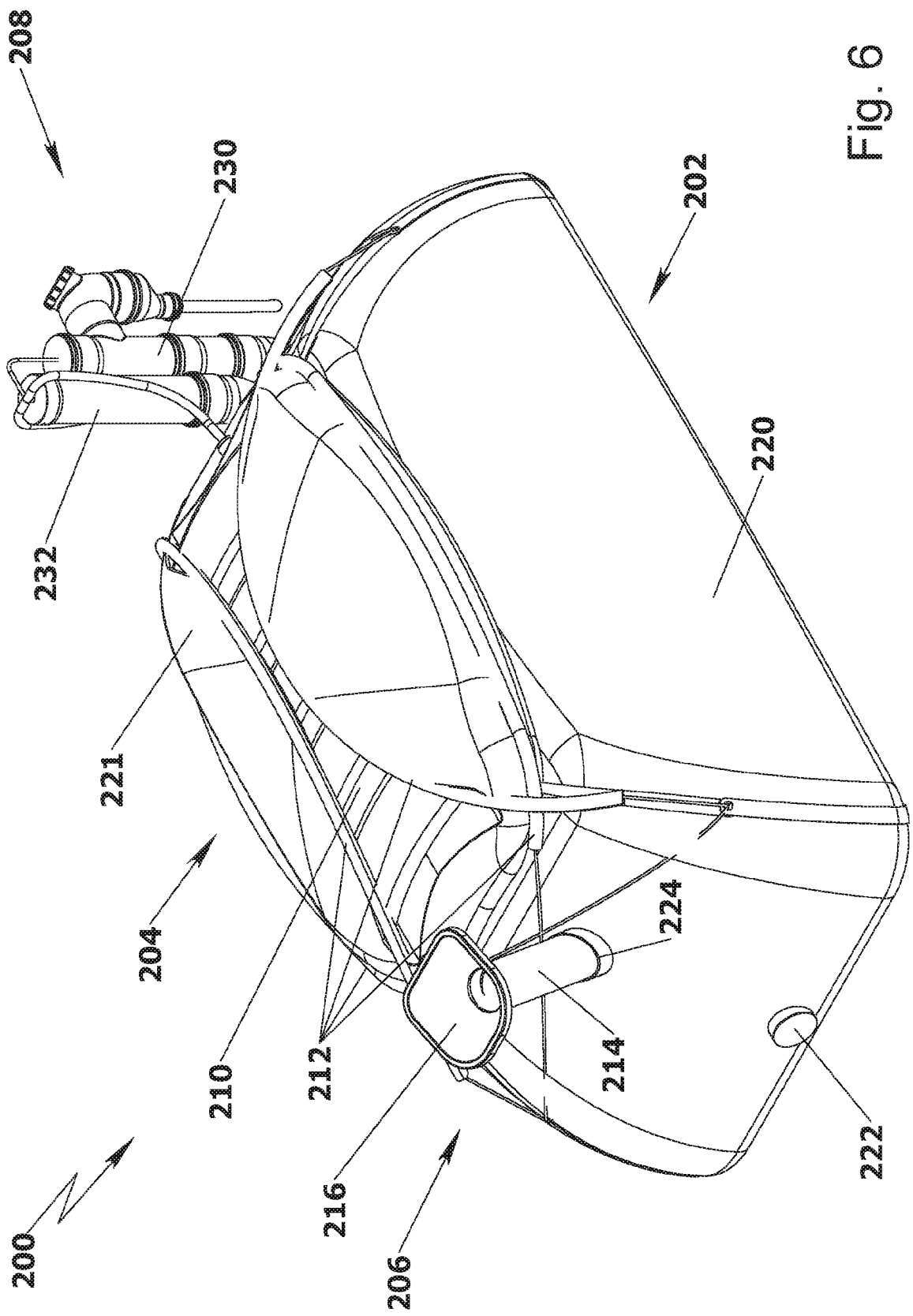
FIG. 6 is an isometric view of a preferred embodiment of the lightweight or extremely lightweight assemblable appliance, wherein the anaerobic digester is in a deployed or erected configuration, whereas the gas tank in a depleted or collapsed configuration.
Figure 7:
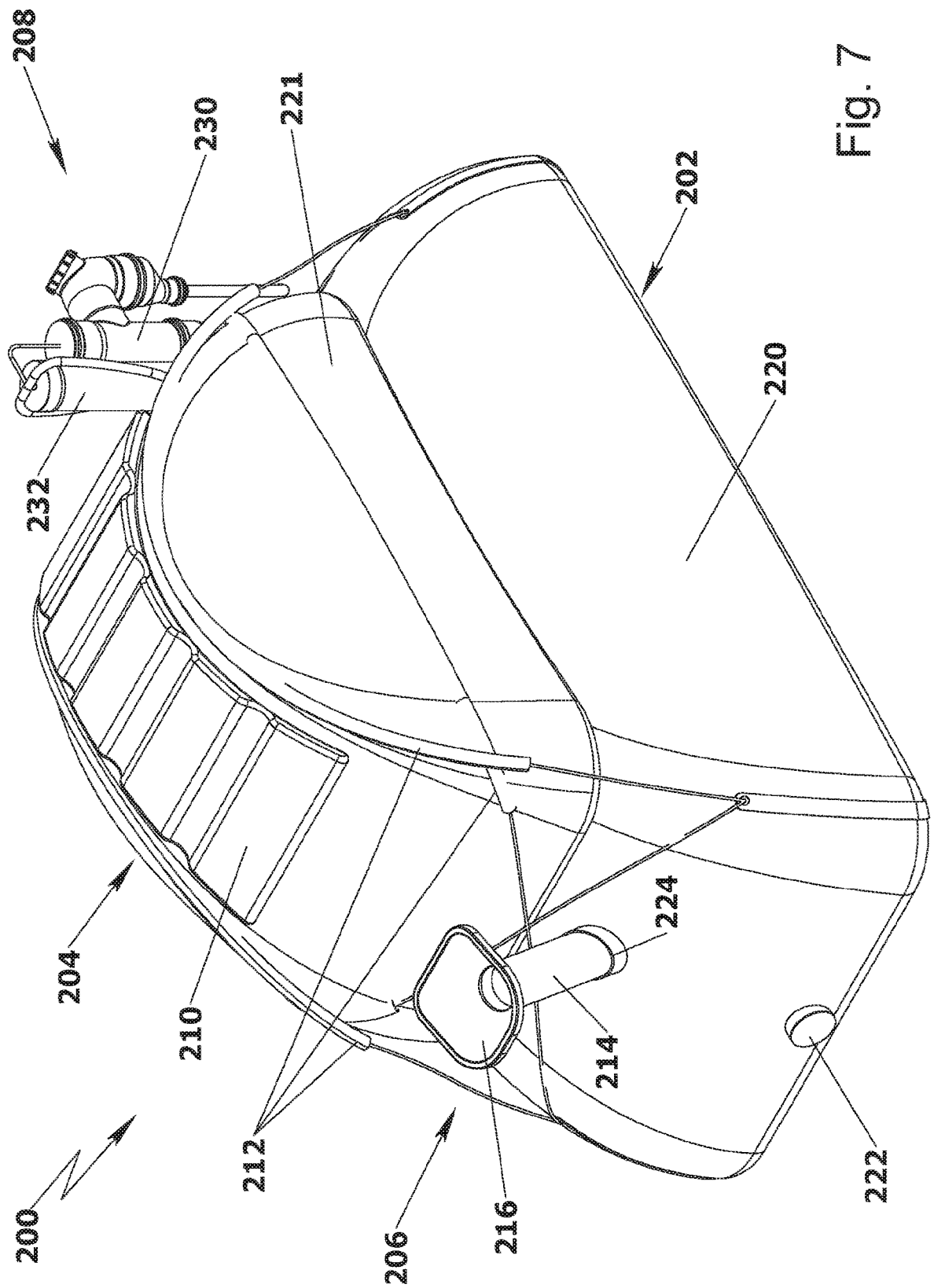
FIG. 7 is an isometric view of a preferred embodiment of the lightweight or extremely lightweight assemblable appliance, supported and shaped by a pliant structured exoskeletal envelope.

In accordance with some preferred embodiments of the present invention, reference is now made to FIGS. 5 to 7, showing isometric views of lightweight or preferably extremely lightweight assemblable appliance 200. Appliance 200 comprises anaerobic digester 202 and gas tank 204. Digester 202 and tank 204 are made of elastic, resilient or pliable material.

Appliance 200 further comprises pliant structured exoskeletal envelope 220 for anaerobic digester 202 and pliant structured exoskeletal envelope 221 for gas tank 204. Pliant structured exoskeletal envelops 220 defines a frusto-pyramidal shape, where anaerobic digester 202 is accommodated, whereas pliant structured exoskeletal envelope 221 defines a frusto-pyramidal shape, where gas tank 104 is accommodated. Pliant structured exoskeletal envelopes 220 and 221 respectively confine digester 202 and tank 204, thereby limiting the expansion thereof.

Consequently, upon filling-up anaerobic digester 202 with semiliquid mixture or slurry or ground organic matter or any type of fluid for that matter, in a non-limiting manner including water, grey water and slurry overflow fluid, and/or upon forming positive pressure in gas tank 204, pliant structured exoskeletal envelopes 220 and 221 are expanded and shaped-up by the pressure exerted from within by digester 202 and tank 204, to assume an erected or deployed confirmation, shown in FIG. 7. It is noted that the anaerobic digestion processes, occurring in pliable anaerobic digester 202, resulting a positive pressure in gas tank 204, mainly of methane gas. In some embodiments, organic matter optionally includes for animal droppings, which utilized by lightweight assemblable appliance 200, typically without grinding.

Upon filling-up anaerobic digester 202 with content and forming positive pressure in gas tank 204, pliant structured exoskeletal envelope 220 and 221 confer structural firmness to appliance 200, due to a normal counterforce to the force exerted by the faces of digester 202 and tank 204 on exoskeletal envelopes 220 and 221, somewhat resembling the structural firmness of a wheel tire (not shown) conferred by the expansion of the inner tube (not shown). Pliant exoskeletal envelopes 220 and 221 embody structured shapes, configured to accommodate anaerobic digester 202 and gas tank 204, so as to limit their expansion to a maximal predetermined size.

Pliant exoskeletal envelopes 220 and 221 are preferably made of woven or fibrous fabric, having high tensile strength and capable of being efficiently flexed or bent but incapable of being efficiently stretched or expanded. In some embodiments, pliant structured exoskeletal envelopes 220 and 221 are co-molded or welded with anaerobic digester 202 and/or gas tank 204, to form a monolithic constituent, in which anaerobic digester 202 and/or gas tank 204 are non-detachable pliant structured exoskeletal envelopes 220 and 221.

In some preferred embodiments, pliant structured exoskeletal envelopes 220 and 221 are co-molded or welded with anaerobic digester 202 and/or gas tank 204, so that envelopes 220 and 221 as well as digester 202 and/or gas tank 204 comprise composite materials. A preferred instance of composite material used for manufacture the complex of exoskeletal envelope 220 and anaerobic digester 202 is a multilayered PVC sheet with embedded nylon or other polymeric pliable fibers.

In some embodiments, pliant structured exoskeletal envelopes 220 and 221 are a unified singular pliant structured exoskeletal envelope, such as envelope 120 shown in FIGS. 2 to 4. In other embodiments, pliant structured exoskeletal envelopes 220 and 221 are individual constituents distinct from anaerobic digester 202 and/or gas tank 204.

Anaerobic digester 202 comprises anterior flange 224, configured for connecting and mounting anterior inlet assembly 206, implementable for feeding semiliquid mixture, slurry, ground organic matter or a fluid, into anaerobic digester 202. Anterior flange 224 preferably comprises a feeding mechanism, such as a diaphragm or mitral valve (not shown), configured to sustain advancement of semiliquid mixture, slurry, ground organic matter or a fluid, fed into anaerobic digester 202, from anterior inlet assembly 206 but concurrently configured to prevent backflow of the contents from digester 202 into anterior inlet assembly.

Anaerobic digester 202 comprises posterior flanges 226, configured for connecting and mounting posterior outlet assembly 208, implementable for draining grey water or overflow slurry fluid from anaerobic digester 202 as well as for conducting the biogas produced by the anaerobic processes in digester 202 to gas tank 204. Anaerobic digester 202 comprises anterior opening 222 with removable plug, configured for occasionally depleting the sludge that may accumulate in digester 202, as a part of maintenance of lightweight assemblable appliance 200.

In order to yet further facilitate an increased pressure inside gas tank 204, appliance 200 further comprises at least one pressure forming mechanism. Embodiments of pressure forming mechanisms in a non-limiting manner include gravitational and/or bias driven devices. Examples of gravitational devices include array of ballast bags or pockets 210, fillable with ballast substance (not shown), configured to facilitate increased pressure by exerting a gravitational force onto gas tank 204.

Examples of bias driven devices include elastic tension straps 212, comprising an elastomeric material, connected to respective elements attached to the bottom of appliance 200, configured to facilitate increased pressure by exerting tensile strain force onto inside gas tank 204. Notably a combination of gravitational and/or bias driven devices is equally contemplated by this disclosure.

Anterior inlet assembly 206 comprises feeding conduit 214, which is optionally made of solid, stiff or firm material, capable of supporting its own weight. Feeding conduit 214 terminates with inlet funnel 216, preferably coverable by pivoting and preferably biased lid (not shown). In some examples feeding conduit 214 is made of flexible or pliant material, incapable of supporting its own weight, in such cases inlet funnel 216 is supported by a bipod (not shown) structure.

Posterior outlet assembly 208 comprises slurry overflow outlet portion 230 and gas ducting portion 232. Slurry overflow outlet portion 230 preferably comprises a chlorinator (not shown) with a chlorinator filling port and a slurry overflow nozzle. The slurry overflow nozzle is disposed downstream to the chlorinator (not shown), so that any overflow of slurry from digester 202 to outlet portion 230 passes through the chlorinator (not shown), thereby rendering the fluids outflowing from the slurry nozzle non-virulent and biologically safe for the environment or use for irrigation in agriculture.

Gas ducting portion 232 of posterior outlet assembly 208 further comprises biogas filter (not shown), configured for absorbing sulfurous compounds from the biogas produced in anaerobic digester 202. The biogas filter (not shown) optionally comprises activated carbon or activated charcoal, which is replaceable from the top opening covered by a plug (not shown). Gas infiltrating through a biogas filter (not shown) is supplied into gas piping (not shown). The gas piping (not shown) extends from gas ducting portion 232 of posterior outlet assembly 208 to the gas inlet (not shown) of gas tank 204. The gas piping (not shown) further extends to a gas-powered consuming appliance (not shown). The gas piping (not shown) further optionally extends into slurry overflow outlet portion 230. The gas piping further (not shown) optionally comprises check valves, configured to conduct the biogas only in one direction, and/or safety valves, configured to conduct the biogas only above a predetermined pressure threshold.

Reference is now made to FIG. 5, showing the lightweight or preferably extremely lightweight assemblable appliance 200 in folded or collapsed conformation. Lightweight assemblable appliance 200 in folded conformation, shown in FIG. 5, is configured for assuming a compact size. Lightweight assemblable appliance 200, shown in FIG. 5, in folded conformation is typically folded yet further laterally or rolled up to assume a compact size (not shown), configured for shipment and transportation at the back seat of an economy car and/or by air cargo.

Reference is now made to FIG. 6, showing the lightweight or preferably extremely lightweight assemblable appliance 200 in a partially erected or deployed conformation. Lightweight assemblable appliance assumes a partially erected or deployed conformation, shown in FIG. 6, upon filling-up anaerobic digester 202 with liquid. Gas tank 204 of lightweight assemblable appliance 200 in a partially erected or deployed conformation, shown in FIG. 6, is empty of biogas. With the progression of anaerobic processes in anaerobic digester 202, biogas filling-up gas tank 204 and lightweight assemblable appliance 200 assumes completely erected or deployed conformation, shown in FIG. 7.

Figure 8:
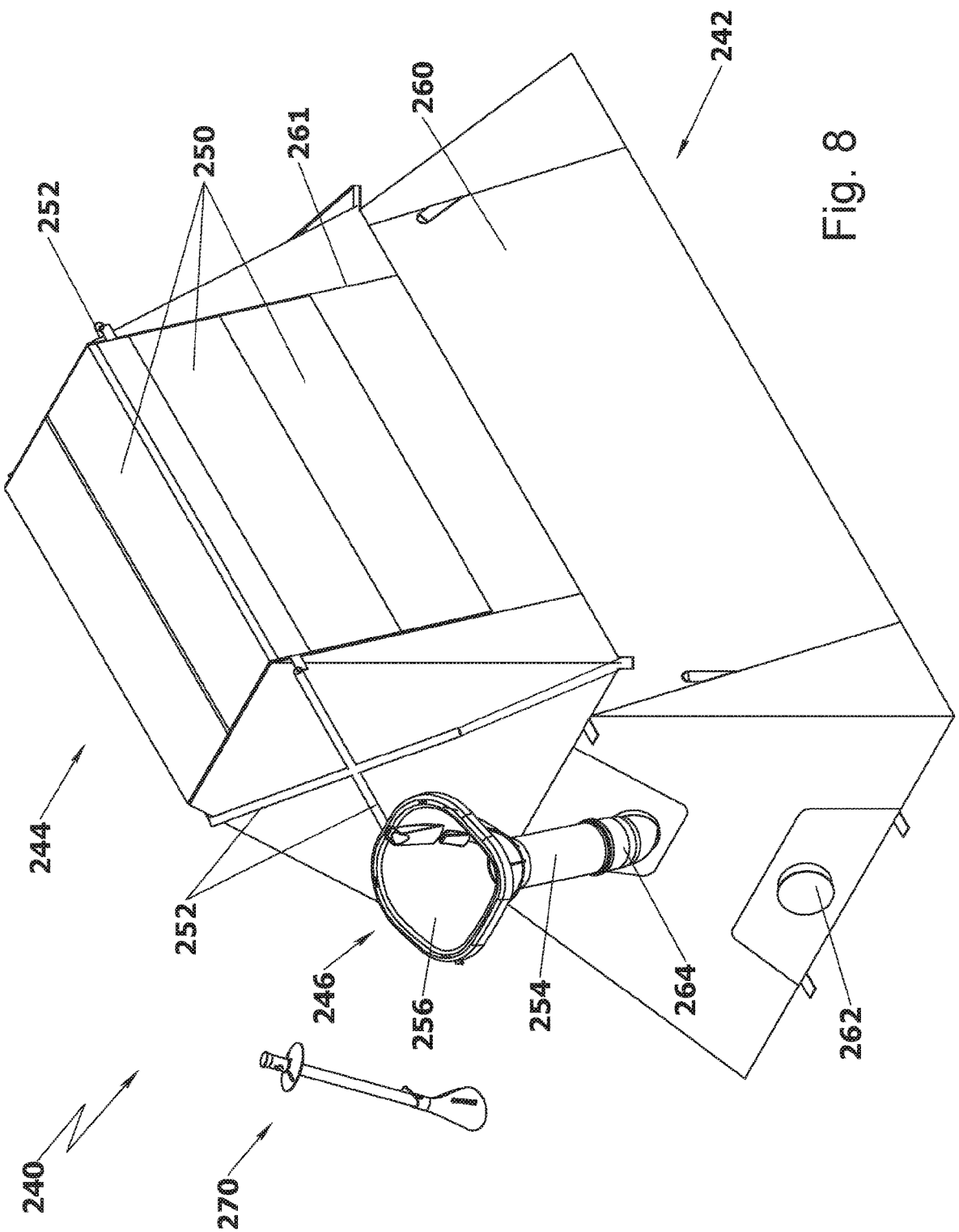
FIG. 8 is an isometric view of another preferred embodiment of extremely lightweight assemblable appliance, supported and shaped by a pliant structured exoskeletal envelope.

Reference is now made to FIG. 8, showing another preferred embodiment of extremely lightweight assemblable appliance 240. Appliance 240 comprises anaerobic digester 242 supported and shaped by pliant structured exoskeletal envelope 260 and gas tank 244 supported and shaped by pliant structured exoskeletal envelope 261. Pliant structured exoskeletal envelopes 260 and 261 respectively confine digester 242 and tank 244, thereby limiting the expansion thereof.

In order to yet further facilitate an increased pressure inside gas tank 244, appliance 240 further comprises at least one pressure forming mechanism, such as array of ballast bags or pockets 250, fillable with ballast substance (not shown), and/or elastic tension straps 252, comprising an elastomeric material, connected to respective elements attached to the bottom of appliance 240, configured to facilitate increased pressure by exerting tensile strain force onto inside gas tank 244. Notably tension straps 252 are attached to the bottom portion of pliant structured exoskeletal envelope 261 enclosing gas tank 244; thereby exerting the tensile strain force only onto gas tank 244.

Anaerobic digester 242 comprises anterior flange 264, configured for connecting and mounting anterior inlet assembly 246, implementable for feeding semiliquid mixture, slurry, ground organic matter or a fluid, into anaerobic digester 242. Anterior inlet assembly 246 comprises feeding conduit 254, typically made of solid, stiff or firm material. Feeding conduit 254 terminates with inlet funnel 256. Anterior inlet assembly 246 preferably comprises a feeding mechanism, such as plunger 270, configured to sustain advancement of semiliquid mixture, slurry, ground organic matter or a fluid, fed into anaerobic digester 242, from anterior inlet assembly 246.

Reference is now made to FIG. 9 showing plunger handle 270 in greater details as well as to FIG. 10A-C showing constituents thereof. Plunger handle 270 comprises handle 272 shown in FIG. 10A, shaft 274 shown in FIG. 10B and terminal part 276 shown in FIG. 10C. Handle 272 comprises proximal portion 278, configured for manual gripping. Handle 272 further comprises conduits 282, configured for conduct air from anterior inlet assembly 246, thereby avoiding back splash from inlet assembly 246 and/or anaerobic digester 242, upon advancing a semiliquid mixture, slurry, ground organic matter or fluid, fed into anaerobic digester 142.

Handle 272 comprises plug 280, configured blocking the opening of feeding conduit 254 at the bottom of inlet funnel 256. Shaft 274 comprises essentially hollow firm pipe 284, defining interior lumen 284, configured for conducting the air from anterior inlet assembly 246, upon advancing the semiliquid mixture or fluid into anaerobic digester 242. Terminal part 276, shown in FIG. 10C, comprises a frusto-conical mitral skirt 288, configured for advancing the semiliquid mixture or fluid into feeding conduit 254, while concurrently preventing backflow of the contents from digester 242 into anterior inlet assembly 246. The top portion of terminal part 276 embodies hanging hook 290 configured for hanging plunger handle 270 from inlet funnel 256 and defines air inlet, configured for conducting the air from anterior inlet assembly 246 into pipe 284, upon advancing the semiliquid mixture or fluid into anaerobic digester 242.

Figure 11A:
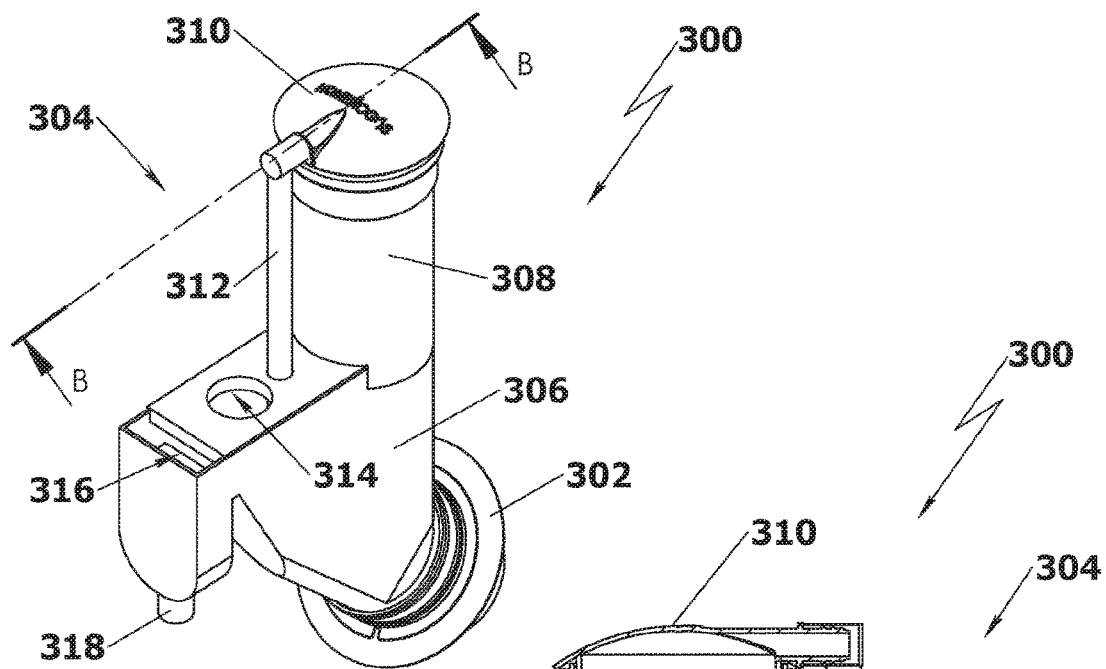
FIG. 11A is an isometric view of a preferred embodiment of combined posterior assembly.
Figure 11B:
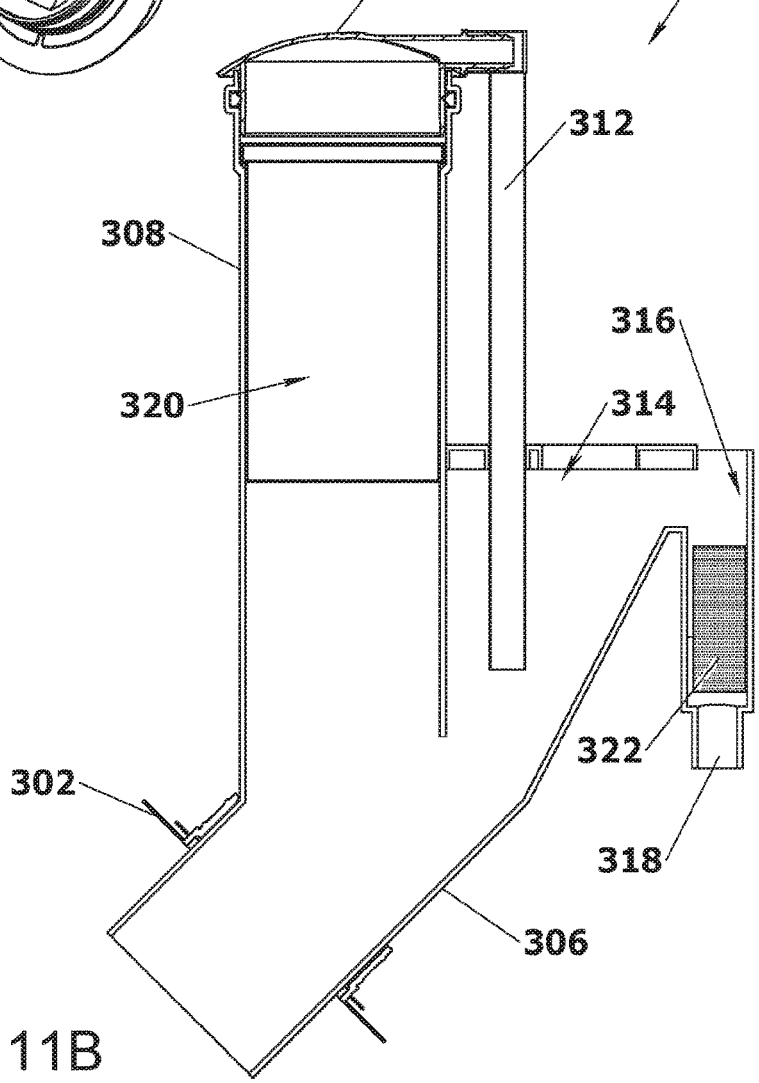
FIG. 11B is a cross-sectional view of the preferred embodiment of combined posterior assembly.

Reference is now made to FIGS. 11A and 11B, showing a preferred embodiment of combined posterior assembly 300. Posterior assembly 300 is mounted onto posterior outlet flange 302, attached to anaerobic digester (not shown), such as anaerobic digester 242 shown in FIG. 8. Posterior assembly 300 comprises slurry overflow outlet portion 306 and gas ducting portion 308. Slurry overflow outlet portion 306 comprises chlorinator 322, chlorinator filling port 316 and slurry overflow nozzle 318. Slurry overflow nozzle 318 is disposed downstream to chlorinator 322. Slurry overflow outlet portion 306 further comprises surplus overflow opening 314, for any excessive slurry overflow that is not drained via nozzle 318.

Gas ducting portion 308 of posterior outlet assembly 300 further comprises gas filter lumen 320. Gas filter lumen 320 configured to contain a substance, such as activated charcoal (not shown), absorbing sulfurous compounds from the biogas, which is replaceable from the top opening covered by plug 310. Gas piping 312 preferably extends into slurry overflow outlet portion 306.

Wherever in the specification hereinabove and in claims hereunder it is noted that the pliable collapsible anaerobic digester, such as digesters 50, 102, 202 or 242, including or comprising an inlet pipe, gas outlet pipe, slurry overflow outlet pipe or sludge outlet draining pipe—it should be construed that the pliable collapsible anaerobic digester includes or comprises merely a preparation on the surface thereof and/or inside the wall thereof as well as an additional element for relatively easily mounting and/or attaching an inlet pipe, gas outlet pipe, slurry overflow outlet pipe or sludge outlet draining pipe thereto, whereas the inlet pipe, gas outlet pipe, slurry overflow outlet pipe or sludge outlet draining pipe are not provided or attached to the digester.

It will be appreciated by persons skilled in the art that the present invention is not limited by what has been particularly shown and described herein above. Rather the scope of the invention is defined by the claims which follow:

The invention claimed is:

1. An assemblable appliance for recycling organic waste into biogas and liquid fertilizer, implementing essentially anaerobic digestion processes, as an autonomic standalone unit, configured for transportation in a compact form, said assemblable appliance comprises:
   (a) a pliant material, characterized by a relatively high tensile strength;
   (b) a pliable material characterized by a relatively low tensile strength;
   wherein said relatively low tensile strength of said pliable material is lower than said relatively high tensile strength of said pliant material;
   (c) a collapsible anaerobic digester disposed at a bottom portion of said assemblable appliance comprising:
      (I) a structured shape;
      (II) at least one tensile element, made of said pliant material having said relatively high tensile strength;
      (III) a sheeting element forming an essentially closed structure, made of said pliable material having said relatively low tensile strength;
      (IV) a plurality of apertures for connectors of said appliance comprising:
         (i) an inlet configured for feeding a semiliquid mixture of organic matter and water into anaerobic digester;
         (ii) a gas outlet, hermetically attached to an upper portion of said anaerobic digester;
         (iii) a slurry overflow outlet, extending from a sidewall of said anaerobic digester;
   (d) a collapsible gas tank disposed at a top portion of said assemblable appliance comprising:
      (I) a structured shape;
      (II) at least one tensile element made of said pliant material having said relatively high tensile strength;
      (III) a sheeting element forming an essentially closed structure, made of said pliable material, having said relatively low tensile strength;
      (IV) at least one aperture selected from the group consisting of: a gas inlet and gas outlet;
   (b) at least one pressure exerting mechanism, configured to facilitate increased pressure in said collapsible gas tank, selected from the group consisting of:
      (I) elastic tension straps, comprising an elastomeric material, connectable to connectors elements attached to said appliance, and
      (II) a flexible elongated and foldable ballast bag, fillable with ballast substance, said flexible elongated ballast bag is capable of assuming a conformation, respectively matching the shape of said collapsible gas tank;
said assemblable appliance is characterized by lacking any rigid structural support scaffolding.

2. The assemblable appliance, as set forth in claim 1, further comprises at least one component, of a feeding sub-assembly, selected from the group consisting of:
   (a) a feeding conduit comprising a solid, stiff or firm material, capable of supporting its own weight, connected to inlet of said collapsible anaerobic digester;
   (b) a feeding conduit comprising a flexible or pliant material, incapable of supporting its own weight, in combination with a support structure;
   (c) a feeding funnel configured for feeding said organic waste into said feeding conduit;
   (d) a grinder, configured to grind said organic waste into said semiliquid mixture;
   (e) a sink cover characterized by a sloped or slated shape, thereby facilitating feeding said organic waste into said anaerobic digester;
   (f) a water canister, for supplying a water fraction for said semiliquid mixture; and
   (g) a water tap for controlling the amount of said water fraction in said semiliquid mixture.

3. The assemblable appliance, as set forth in claim 1, further comprises a means for feeding said semiliquid mixture under pressure into said inlet of said collapsible anaerobic digester.

4. The assemblable appliance, as set forth in claim 1, wherein said structured shape of said collapsible anaerobic digester and of said collapsible gas tank is a frusto-pyramidal or frusto-conical structured shape.

5. The assemblable appliance, as set forth in claim 1, wherein said gas outlet and said slurry overflow outlet of said anaerobic digester are essentially a unified singular opening in said anaerobic digester.

6. The assemblable appliance, as set forth in claim 1, wherein said tensile element, of said collapsible anaerobic digester and/or said collapsible gas tank, is co-molded with or welded to or fused with or reinforcing said sheeting element of said collapsible anaerobic digester and/or said collapsible gas tank; thereby forming an essentially unified or monolithic structure.

7. The assemblable appliance, as set forth in claim 1, further comprises least one element selected from the group consisting of:
  (a) an external structured tensile envelope configured for enclosing said collapsible anaerobic digester, wherein said external structured tensile envelope for enclosing said collapsible anaerobic digester is made of said pliant material, having said relatively high tensile strength;
  (b) an external structured tensile envelope configured for enclosing said collapsible gas tank, wherein said external structured tensile envelope for enclosing said collapsible gas tank is made of said pliant material, having said relatively high tensile strength; and
  (c) an external structured tensile envelope configured for enclosing in combination said collapsible anaerobic digester and said collapsible gas tank, wherein said external structured tensile envelope for enclosing in combination said collapsible anaerobic digester and said collapsible gas tank is made of said pliant material, having said relatively high tensile strength.

8. A method of recycling organic waste into biogas and liquid fertilizer, implementing essentially anaerobic digestion processes, by a means of assemblable appliance, as an autonomic standalone unit, said method comprises:
  (a) providing a compact kit-of-parts, configured for transportation in a folded form, said kit-of-parts comprising:
    (I) a pliant material, characterized by a relatively high tensile strength;
    (II) a pliable material characterized by a relatively low tensile strength;
    wherein said relatively low tensile strength of said pliable material is lower than said relatively high tensile strength of said pliant material;
    (III) a collapsible anaerobic digester disposed at a bottom portion of said assemblable appliance comprising:
      (i) a structured shape;
      (ii) at least one tensile element made of said pliant material having said relatively high tensile strength;
      (iii) a sheeting element forming an essentially closed structure, made of said pliable material, having said relatively low tensile strength;
      (iv) a plurality of apertures for connectors of said appliance comprising:
        an inlet configured for feeding a semiliquid mixture of organic matter and water into said anaerobic digester;
        at least one outlet, extending from a sidewall of said anaerobic digester;
    (IV) a collapsible gas tank disposed at a top portion of said assemblable appliance comprising:
      (i) a structured shape;
      (ii) at least one tensile element made of said pliant material having said relatively high tensile strength;
      (iii) a sheeting element forming an essentially closed structure, made of said pliable material, having said relatively low tensile strength;
      (iv) at least one element selected from the group consisting of: a gas inlet and gas outlet;
    (V) at least one pressure exerting mechanism, configured to facilitate increased pressure in said collapsible gas tank, selected from the group consisting of:
      (i) elastic tension straps, comprising an elastomeric material, connectable to connectors elements attached to said appliance, and
      (ii) a flexible elongated and foldable ballast bag, fillable with a ballast substance, said flexible elongated ballast bag is capable of assuming a conformation, respectively matching the shape of said collapsible gas tank;
  wherein said assemblable appliance is characterized by lacking any rigid structural support scaffolding;
    (b) assembling said lightweight structural appliance from said kit-of-parts;
    (c) feeding a semiliquid mixture or slurry of ground organic matter and water into said collapsible anaerobic digester;
    (d) sustaining essentially anaerobic digestion processes in said collapsible anaerobic digester;
  wherein said assemblable appliance is characterized by lacking any rigid structural support scaffolding.

9. The method of recycling organic waste, as set forth in claim 8, wherein said assemblable appliance further comprises at least one component, of a feeding sub-assembly, selected from the group consisting of:
  (a) a feeding conduit comprising a solid, stiff or firm material, capable of supporting its own weight, connected to inlet of said collapsible anaerobic digester;
  (b) a feeding conduit comprising a flexible or pliant material, incapable of supporting its own weight, in combination with a support structure;
  (c) a feeding funnel configured for feeding said organic waste into said feeding conduit;
  (d) a grinder, configured to grind said organic waste into said semiliquid mixture;
  (e) a sink cover characterized by a sloped or slated shape, thereby facilitating feeding said organic waste into said anaerobic digester;
  (f) a water canister, for supplying a water fraction for said semiliquid mixture; and
  (g) a water tap for controlling the amount of said water fraction in said semiliquid mixture.

10. The method of recycling organic waste, as set forth in claim 8, further comprises a means for feeding said semiliquid mixture under pressure into said inlet of said collapsible anaerobic digester.

11. The method of recycling organic waste, as set forth in claim 8, wherein said structured shape of said collapsible anaerobic digester and of said collapsible gas tank is a frusto-pyramidal or frusto-conical structured shape.

12. The method of recycling organic waste, as set forth in claim 8, wherein said gas outlet and said outlet of said anaerobic digester are essentially a unified singular opening in said anaerobic digester.

13. The method of recycling organic waste, as set forth in claim 8, wherein said tensile element is co-molded with or welded to said sheeting element of at least one member selected from the group consisting of: said anaerobic digester and said gas tank; thereby forming an essentially unified or monolithic structure with said at least one member.

14. The method of recycling organic waste, as set forth in claim 8, wherein said lightweight structural appliance further comprises at least one element selected from the group consisting of:
  (a) an external structured tensile envelope configured for enclosing said collapsible anaerobic digester, wherein said external structured tensile envelope for enclosing said collapsible anaerobic digester is made of said pliant material, having said relatively high tensile strength;
(b) an external structured tensile envelope configured for enclosing said collapsible gas tank, wherein said external structured tensile envelope for enclosing said collapsible gas tank is made of said pliant material, having said relatively high tensile strength; and
(c) an external structured tensile envelope configured for enclosing in combination said collapsible anaerobic digester and said collapsible gas tank, wherein said external structured tensile envelope for enclosing in combination said collapsible anaerobic digester and said collapsible gas tank is made of said pliant material, having said relatively high tensile strength.

15. A compact kit-of-parts of an assemblable appliance for recycling organic waste into biogas and liquid fertilizer, implementing essentially anaerobic digestion processes, as an autonomic standalone unit, configured for transportation in a compact form, said kit-of-parts comprises:
(a) a pliant material, characterized by a relatively high tensile strength;
(b) a pliable material, characterized by a relatively low tensile strength;
  wherein said relatively low tensile strength of said pliant material is lower than said relatively high tensile strength of said pliable material;
(c) a collapsible anaerobic digester disposed at a bottom portion of said assemblable appliance comprising:
  (I) a structured shape;
  (II) at least one tensile component made of said plaint material having said relatively high tensile strength;
  (III) a sheeting component forming an essentially closed structure, made of said pliable material, having said relatively low tensile strength;
  (IV) a plurality of apertures for connectors of said appliance;
    (i) an inlet configured for feeding a semiliquid mixture of organic matter and water into said anaerobic digester;
    (ii) at least one outlet, extending from a sidewall of said anaerobic digester;
(d) a collapsible gas tank disposed at a top portion of said assemblable appliance comprising:
  (I) a structured shape;
  (II) at least one tensile component made of said plaint material having said relatively high tensile strength;
  (III) a sheeting component forming an essentially closed structure, made of said pliable material, having said relatively low tensile strength;
  (IV) at least one element selected from the group consisting of: a gas inlet and gas outlet;
(e) at least one pressure exerting mechanism, configured to facilitate increased pressure in said collapsible gas tank, selected from the group consisting of:
  (I) elastic tension straps, comprising an elastomeric material, connectable to connectors elements attached to said appliance, and
  (II) a flexible elongated and foldable ballast bag, fillable with ballast substance, said flexible elongated ballast bag is capable of assuming a conformation, respectively matching the shape of said collapsible gas tank;
wherein said compact kit-of-parts of said assemblable appliance is characterized by lacking any rigid structural support scaffolding.

16. The kit-of-parts, as set forth in claim 15, further comprises at least one component, of a feeding sub-assembly, selected from the group consisting of:
(a) a feeding conduit comprising a solid, stiff or firm material, capable of supporting its own weight, connected to inlet of said collapsible anaerobic digester;
(b) a feeding conduit comprising a flexible or pliant material, incapable of supporting its own weight, in combination with a support structure;
(c) a feeding funnel configured for feeding said organic waste into said feeding conduit;
(d) a grinder, configured to grind said organic waste into said semiliquid mixture;
(e) a sink cover characterized by a sloped or slated shape, thereby facilitating feeding said organic waste into said anaerobic digester;
(f) a water canister, for supplying a water fraction for said semiliquid mixture; and
(g) a water tap for controlling the amount of said water fraction in said semiliquid mixture.

17. The kit-of-parts, as set forth in claim 15, further comprises a means for feeding said semiliquid mixture into said inlet of said collapsible anaerobic digester.

18. The kit-of-parts, as set forth in claim 15, wherein said structured shape of said collapsible anaerobic digester and of said collapsible gas tank is a frusto-pyramidal or frusto-conical structured shape.

19. The kit-of-parts, as set forth in claim 15, wherein said tensile component is co-molded with or welded to said sheeting component of at least one member selected from the group consisting of: said anaerobic digester and said gas tank;
thereby forming an essentially unified or monolithic structure with said at least one member.

20. The kit-of-parts, as set forth in claim 15, further comprises at least one element selected from the group consisting of:
(a) an external structured tensile envelope configured for enclosing said collapsible anaerobic digester, wherein said external structured tensile envelope for enclosing said collapsible anaerobic digester is made of said pliant material, having said relatively high tensile strength;
(b) an external structured tensile envelope configured for enclosing said collapsible gas tank, wherein said external structured tensile envelope for enclosing said collapsible gas tank is made of said pliant material, having said relatively high tensile strength; and
(c) an external structured tensile envelope configured for enclosing in combination said collapsible anaerobic digester and said collapsible gas tank, wherein said external structured tensile envelope for enclosing in combination said collapsible anaerobic digester and said collapsible gas tank is made of said pliant material, having said relatively high tensile strength.

* * * * *